US006960678B2

(12) United States Patent  
Sieburth et al.

(10) Patent No.: US 6,960,678 B2  
(45) Date of Patent: Nov. 1, 2005

(54) SILANOL ENZYME INHIBITORS

(75) Inventors: Scott McN. Sieburth, Coram, NY (US); Alfred M. Mutahi, Edison, NJ (US); Chien-An Chen, Madison, WI (US)

(73) Assignee: The Research Foundation of State University of New York, Albany, NY (US)

( * ) Notice: Subject to any disclaimer, the term of this patent is extended or adjusted under 35 U.S.C. 154(b) by 323 days.

(21) Appl. No.: 10/171,560

(22) Filed: Jun. 11, 2002

(65) Prior Publication Data

US 2003/0096793 A1 May 22, 2003

Related U.S. Application Data

(62) Division of application No. 09/194,715, filed on Dec. 17, 1998, now Pat. No. 6,441,212, which is a continuation-in-part of application No. PCT/US97/12041, filed on Jul. 11, 1997, which is a continuation of application No. 08/680,330, filed on Jul. 12, 1996, now Pat. No. 5,760,019.

(51) Int. Cl.$^7$ ................................................. C07F 7/02
(52) U.S. Cl. ...................... 556/400; 556/411; 556/413; 556/418; 556/419; 556/425; 556/436; 562/553; 514/63
(58) Field of Search ................................ 556/400, 411, 556/413, 418, 419, 425, 436; 562/553; 514/63

(56) References Cited

U.S. PATENT DOCUMENTS

| | | | |
|---|---|---|---|
| 3,860,709 A | 1/1975 | Abbott et al. ................. 514/63 |
| 4,328,216 A | 5/1982 | Toyoshima et al. ........... 514/63 |
| 4,420,475 A | 12/1983 | Damon, II .................... 514/63 |
| 4,898,977 A | 2/1990 | Herold et al. ................ 564/191 |
| 4,927,952 A | 5/1990 | Gueyne et al. ............. 556/419 |
| 4,985,405 A | 1/1991 | Gueyne et al. ................ 514/8 |
| 5,037,803 A | 8/1991 | Gueyne et al. ................ 514/2 |
| 5,045,537 A | 9/1991 | Weidmann ................... 514/63 |
| 5,087,452 A | 2/1992 | Gueyne et al. ............. 426/422 |
| 5,142,056 A | 8/1992 | Kempe et al. ............. 546/265 |
| 5,215,968 A | 6/1993 | Nickel et al. ................ 514/19 |
| 5,401,722 A | 3/1995 | Juraszyk et al. ............. 514/18 |
| 5,545,750 A | 8/1996 | Kempf et al. ............... 564/360 |

FOREIGN PATENT DOCUMENTS

EP        0402646      12/1990

OTHER PUBLICATIONS

Andrianov Chem. Abstr. 55:9316h.*
Golubkov Chem. Abstr. 54:16059b.*
Wiberg Chem. Abstr. 53: 1204g.*
Andrianov Chem. Abstr. 53: 1204b.*
Otiashvili Chem. Abstr. 127: 220707s, 1997.*
Otiashvili Soobshch. Akad. Nauk Gruz. 152(3), 531–536, 1995.*

Kam, C.M., Wishino, N., Powers, J.C. "Inhibition of Thermolysin and Carboxypeptidase A by Phosphoramidates". *Biochemistry* 1979, 18, 3032–3038.

Amiri, P., Lindquist, R.N., Matteson, D.S., Sadhu, K.M. "Benzamidomethaneboronic Acid: Synthesis and Inhibition of Chymotrypsin". Arch. Biochem Biophys. 1984, 234, 531–536.

Galardy, P.E., Kortylewicz, Z.P., "Inhibitors of Angiotensin-Converting Enzyme Containing a Tetrahedral Arsenic Atom", *Biochem. J.*, 1985, 226, 447–454.

Likiss, P.D., "The Synthesis and Structure of Organosilanois," *Adv. Inorg. Chem.* 1995, 42, 147–262.

Freidberg, K.D., Schiller, E. *Handbook on the Toxicity of Inorganic Compounds.* Seiler, H.G. and Sigel, H., Eds, Marcel Dekker, New York, 1988, pp 595–617.

Schechter, I., Berger, A. "On the Active Site of Protease. III. Mapping The Active Site of Papain; Specific Peptide Inhibitors of Papain." *Biochem. Biophys. Res. Commun.* 1968, 32, 898–902.

Schechter, I., Berger, A. "On the Size of the Active Site in Proteases. I. Papain", *Biochem. Biophys. Res Commun.* 1967, 27, 157–162.

I. Fleming, "Organic Silicon Chemistry" in *Comprehensive Organic Chemistry.* D. Barton, W.D. Ollis, Eds, Pergamon, New York 1979, vol. 3, pp. 576–579.

I. Ojima, "The Hydrosilation Reaction" in *The Chemistry of Organic Silicon Compounds.* S. Patai and Z. Rappoport, Eds., Wiley, New York 1989, vol. 2, pp 1479–1525.

Murai, T., Oda, T., Kimura, F., Onishi, H., T. Kanda, Kato, S., "Rhodium (11) Acetate Catalysed Hydrosilation of Enamides and N–Vinylureas Leading to 1–(Trialkylsilyl) alkylamine Derivatives", *J. Chem. Soc. Chem. Commun.* 1994, 2143–2144.

Beak, P., Zajdel, W.J. Reitz, D.S. "Metalation and Electrophilic Substitution of Amine Derivatives Adjacent to Nitrogen: α–Metallo Amine Synthetic Equivalents", *Chem. Rev.* 1984, 84, 471–523.

(Continued)

*Primary Examiner*—Jon Weber
*Assistant Examiner*—David Lukton
(74) *Attorney, Agent, or Firm*—Hoffman & Baron, LLP

(57) ABSTRACT

Compounds of formula (I, II or III), wherein X is OH; Y is OH, H, lower alkyl of one to six carbons or heteroatoms or F; Z and Z' are independently H, lower alkyl or $Q_3Si$ where Q is lower alkyl or aryl; n is 3–50; n' is 2–50; A and B are independently a) alkyl of one to ten carbons or heteroatoms, b) aryl of four to seven carbons or heteroatoms, c) cyclic of three to ten carbons or heteroatoms, or moieties of the formulas (d, e, or f); $R^1$–$R^{11}$ groups are each independently hydrogen, alkyl of one to ten carbons or heteroatoms, aryl of 4 to 14 carbons or heteroatoms, arylalkyl of five to twenty carbons or heteroatoms; unsubstituted carbonyl or substituted carbonyl. Heteroatoms are nitrogen, oxygen, silicon or sulfur. At least one of A or B, or both A and B are d), e), or f). The compounds of formula (I) inhibit protease enzymes and can be used as pharmaceuticals.

3 Claims, No Drawings

OTHER PUBLICATIONS

Eaborn, C., "Cleavages of Aryl–Silicon and Related Bonds by Electrophiles", *J. Organomet. Chem.* 1975, 100, 43–57.

DeVoss, J.J., Z. Sui, D. DeCamp, R. Salto, L. Babé, C. Craik, P. Ortiz de Monteliano "Haloperidol–Based Irreversible Inhibitors of the HIV–1 and HIV–2 Proteases", *J. Med. Chem.* 1994, 37, 665–673.

Vacca, J.P., "Design of Tight–Binding Human Immunodeficiency Virus Type 1 Protease Inhibitors", *Methods Enzymol.* 1994, 241, 311–334.

Matthews, B.W., "Structural Basis of the Action of Thermolysin And Related Zinc Peptidases", *Acc. Chem. Res.* 1988, 21, 333–340.

Christianson, D.W., Lipscomb, W.M., "Carboxypeptidase A", *Acc. Chem Res.* 1989, 22. 62–69.

Rich, D.H., "Peptidase Inhibitors", in *Comprehensive Medicinal Chemistry*. C. Hansh et al, Ed., Pergamon, New York 1990, pp 391–441.

Fischer, G., "Trends in Protease Inhibition" *National Product Reports* 1988, 5, 465–495.

Gordon, E.M., S. Natarajan, J. Pluscec, H.W. Weller, J.D. Godfrey, M.S. Rom, E.F. Sabo, J. Engebrecht, D.W. Cushman, "Katomethyldipeptides II. Effect of Modification of the α–Aminoketone Portion on Inhibition of Angiotensin Converting Enzyme", *Biochem. Biophys. Res. Commun.* 1984, 124, 148–155.

Bone, R., Sampson, M.S., Bartlett, P.A., Agard, D.A. "Crystal Structure of α–Lytic Protease Complexes With Irreversibly Bound Phosphonate Esters", *Biochemistry* 1991, 30, 2263–2272.

Govardhan, C.P., "Structure– Activity Studies of Flurokentone Inhibitors Abeles, R.H., of α–Lytic Protease and Human Leucocyte Elastase", *Arch. Biochem Biophys.* 1990, 280, 137–146.

Corriu, R.J.P., Guérin, C., Moreau, J.J.E., "Stereochemistry at Silicon", *Topics In Stereochemistry* 1984, 15, 80–103.

R. Tacke, D. Reichel, M. Kropfgans, P.G. Jones, E. Mutschler, J. Gross, X. Hou, M. Waelbroeck, G. Lambrecht, "Biological Recognition of Enantiomeric Silanes: Syntheses And Antimuscarinic Properties of Optically Active (α–Aminoethyl)clyclohexyl(hydroxy methyl) phenylsilanes And Related Quaternary Ammonium Derivatives", *Organometallics* 1995, 14, 251–257.

F. Liebner, U. Bankwitz, Rühlmann, K., Synthese Von Fungicid Wirksamen (1H–α, 4–Triazol–1–yl–methyl) silanen Und—siloxanen, *liebigs Ann. Chem.* 1994, 145–150.

S. Thaisrivongs, " HIV Protease Inhibitors", *Annual Reports In Medicinal Chemistry*. ed. J.A. Bristol, Academic Press, Inc., New York 1994, 29, 133–144.

R. Bone, J.P. Vacca, P.S. Anderson, M.K. Holloway, "X–Ray Crystal Structure of the HIV Protease Complex with L–700, 417, An Inhibitor With Pseudo $C_2$ Symmetry", *Journal of the American Chemical Society*. 1991, 113, 9382–9384.

J.P. Vacca, J.P. Guare, S.J. deSolms, W.M. Sanders, E.A. Giuliani, S.D. Young, P.L. Darke, J. Zugay, I.S. Sigal, W.A. Schleif, J.C. Quintero, E.A. Emini, P.S. Anderson, J.R. Huff, "Benzocycloalkyl Amines As Novel C–Termini For HIV Protease Inhibitors", *Journal of Medicinal Chemistry*. 1991, 34, 228–1230.

I. Fleming, "the Electrophilic Substitution of Allysilanes And Vinylsilanes", *Organic Reactions*. John Wiley & Sons, Inc., New York, 1989, 61.

J.Y. Corey, D.M., Kraichely, J.L. Huhmann, J. Braddock-Wilking, "Reactions of $H(PhMeSi)_3$ H With Triflic Acid: Evidence of Rearrangement Processes", *Organometallics* 1994, 13, 3408–3410.

W. Uhtig, "Zur Darstellung Neuer Organosiliciumpolymere Aus Spezieli Substituierten Silyltriflatderivaten", *Journal of Organometallic Chemistry* 1994, 476, 225–229.

H. Stüger, "Synthese 1,4–disubstitierter Tetrasilane Durch Selektive Spaitung Von Si–Phenyl Bindungen", *Journal of Organometallic Chemistry* 1992, 433, 11–19.

A.R. Bassindale, T. Stout, "The Synthesis Of Functionalized Silytriflates", *Journal of Organometallic Chemistry* 1984, 271, C1–C3.

C. Eaborn, "Organosilicon Compounds. Part I. The Formation Of Alkyliodosilanes", *Journal of the Chemical Society* 1949, 2755–2764.

Tacke, R., Linch, H., "Bioorganosilicon Chemistry" in *The Chemistry of Organic Silicon Compounds*. S. Patai and Z. Rappaport, Eds, John Wiley, New York 1989, pp 1143–1206.

\* cited by examiner

SILANOL ENZYME INHIBITORS

This application is a divisional of, and claims priority to, U.S. application Ser. No. 09/194,715 filed Dec. 17, 1998, now U.S. Pat. No. 6,441,212, which is a continuation-in-part of PCT/US97/12041, filed Jul. 11, 1997, which is a continuation of application Ser. No. 08/680,330, filed Jul. 12, 1996, now U.S. Pat. No. 5,760,019.

The invention relates to silanol-based peptide analogs, their synthesis and their use to inhibit protease enzymes.

BACKGROUND OF THE INVENTION

Protease enzymes mediate many biological processes, e.g., by editing a polypeptide to a shorter, active form, or by terminating biological activity through degradation of an active polypeptide. Other protease enzymes are concerned with tissue remodeling.

Proteases hydrolyze the amide backbone of polypeptides and during this hydrolysis, a tetrahedral intermediate is formed as part of the enzyme-substrate complex. Some analogs of the tetrahedral intermediate can inhibit protease enzymes. Elements other than carbon, specifically, phosphorous and boron, have been used to prepare transition state analogs. Phosphorous: Kam, C.M.; Nishino, N.; Powers, J. C. , "Inhibition of Thermolysin and Carboxypeptidase A by Phosphoraridates", Biochemistry 18, 3032–3038 (1979). Boron: Amiri, P.; Lindquist, R. N.; Matteson, D. S.; Sadhu, K. M. "Benzamidomethaneboronic Acid: Synthesis and Inhibition of Chymotrypsin", Arch. Biochem. Biophys. 234, 531–536 (1984). There has been only one attempt, however, to utilize silanols in transition state analogs because silanediols have a strong proclivity to self condense and form siloxanes or silicones. The simplest silanediol, dimethylsilanediol, was tested as an inhibitor of angiotensin-converting enzyme and found to be inactive. Galardy, R. E.; Kortylewicz, Z. P. "Inhibitors of angiotensin-converting enzyme containing a tetrahedral arsenic atom", Biochem. J. 226, 447–454 (1985). In addition, known silanediols are virtually all dialkyl or diaryl homologues. Lickiss, P. D., "The Synthesis and Structure of Organosilanols", Adv. Inorg. Chem. 42, 147–262 (1995). Therefore, organic silanols have been absent from the field of protease inhibition.

It is an object of the invention to provide silicon-containing enzyme inhibitors.

It is a further object of the invention to provide silanols and silanediols and their siloxane oligomers as bioactive molecules, particularly as inhibitors of hydrolase enzymes.

It is a still further object of the invention to provide a process for the synthesis of silanol and silanediol-based peptide mimics as well as their siloxane oligomers.

It is yet another object to provide a method for inhibiting proteases using silicon-containing peptide analogs.

SUMMARY OF THE INVENTION

The silicon-containing compounds of the invention are represented by formula I, formula II or formula III.

formula I

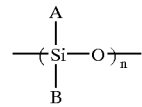
formula II

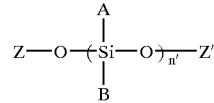
formula III wherein

X is OH;

Y is OH, H, lower alkyl of one to six carbons with said alkyl preferably methyl, or F;

Z and Z' are independently H, lower alkyl with said alkyl preferably methyl or ethyl, or $Q_3Si$ where Q is lower alkyl with said alkyl preferably methyl or ethyl, or Q is aryl of four to ten carbons with said aryl preferably containing phenyl;

n is preferably 3–50, more preferably 3–10, most preferably 3–5;

n' is preferably 2–50, more preferably 2–10, most preferably 2–5;

A and B are independently a) alkyl of one to ten carbons or heteroatoms, preferably three to ten carbons or heteroatoms and said alkyl can be further substituted with aryl;

b) aryl of four to ten carbons or heteroatoms and said aryl can be further substituted with inorganic or organic groups as described below;

c) cyclic of three to ten carbons or heteroatoms;

d)

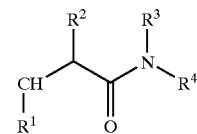

e)

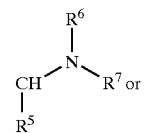

f)

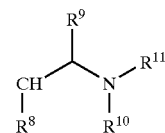

in d, e, and f, CH is bonded to silicon;

$R^1$–$R^{11}$ groups are each independently hydrogen, alkyl of one to ten carbons or heteroatoms, aryl of four to fourteen carbons or heteroatoms, arylalkyl of five to twenty carbons or heteroatoms; substituted carbonyl or unsubstituted carbonyl.

Heteroatoms are nitrogen, oxygen, silicon or sulfur.

$R^3$, $R^4$, $R^6$, $R^7$, $R^{10}$ and $R^{11}$ independently can be one or more naturally-occurring amino acids, e. g. , alanine, asparagine. aspartic acid, cysteine, glutamic acid, phenylalanine, glycine, histidine, isoleucine, lysine, leucine, methionine, proline, glutamine, arginine, serine, threonine, valine, tryptophan and tyrosine. Derivatives of these amino acids, as are known in the art, can also be used.

At least one of A or B, or both A and B, are d), e), or f).

By "independently" is meant that within formulas I–III, all moieties for the variables such as A, B, $R^1$ to $R^{11}$, Z and Z' need not be the same for each variable but may be different moieties within the same compound.

It will also be understood that the compounds have a stable configuration, so that, for example, a destabilizing excess of heteroatoms is not present, and sufficient hydrogens are present to form a stable molecule.

The alkyl groups for A or B may be branched or unbranched and are typically methyl, ethyl, n-butyl, n-propyl, iso-propyl, iso-butyl, iso-pentyl, neo-pentyl, 1-pentyl, 2-pentyl, 3-pentyl, cyclopropylmethyl, and the alkyl groups can be substituted, e.g., with aryl, such as 3-phenyl-1-propyl. The aryl groups for A or B are typically phenyl, phenylmethyl, 1-phenylethyl, 2-phenylethyl, but may also be any other aryl group, for example, pyrrolyl, furanyl, thiophenyl, pyridyl, thiazoyl, imidazoyl, oxazoyl, pyrazinoyl, etc., as well as aryl groups with two or more rings, for example, naphthalenyl, quinolinoyl, isoquinolinoyl, benzothiazoyl, benzofuranyl, etc. The aryl group may also be substituted by an inorganic, alkyl or other aryl group. The cyclic groups for A or B are typically cyclobutylmethyl, cyclopentyl, cyclopentylmethyl. cyclohexyl, cyclohexylmethyl or cycloheptyl.

The alkyl groups for $R^1$ to $R^{11}$ may be branched or unbranched and contain one to ten members including carbon atoms and optional heteroatoms, preferably three to six members including carbon atoms and optional heteroatoms. Some examples of the alkyl groups include methyl, ethyl, n-propyl, isopropyl, n-butyl, sec-butyl, tert-butyl, isobutyl, heptyl, octyl, nonyl and decyl. The alkyl groups may, in whole or in part, be in the form of rings such as cyclopentyl, cyclohexyl, cycloheptyl, cyclohexylmethyl, tetrahydrofuranyl, tetrahydrothiophenyl, tetrahydropyranyl, piperidinyl, pyrrolindinyl, oxazolindinyl, isoxazolidinyl, etc.

Aryl groups for $R^1$–$R^{11}$ typically include phenyl, but may also be any other aryl group, for example, pyrrolyl, furanyl, thiophenyl, pyridyl, thiazoyl, imidazoyl, oxazoyl, pyrazinoyl, etc., as well as aryl groups with two or more rings, for example, naphthalenyl, quinolinoyl, isoquinolinoyl, benzothiazoyl, benzofuranyl, etc. The aryl group may also be substituted by an inorganic, alkyl or other aryl group.

The arylalkyl groups for $R^1$–$R^{11}$ may be any combination of the alkyl and aryl groups described above. These groups may be further substituted. Carbonyl groups for $R^1$–$R^{11}$, can also be substituted, e.g., with alkyl, aryl, or substitute heteroatoms including oxygen, nitrogen and sulfur.

Alkyl, aryl and cyclic groups in all cases (A, B, R, Z and Z') can contain one or more double or triple bonds; and/or their hydrogens may be substituted for by inorganic groups such as amino, thio, halo, doubly bonded oxygen (carbonyl) or singly bonded oxygen (hydroxy) or may be substituted for by organic groups such as alkyl, alkenyl or aryl as described herein.

The compounds are stable and can be stored for weeks or longer at room temperature without noticeable decomposition in either solid or solution form. In addition, there is no intrinsic toxicity associated with silicon (Friedberg, K. D. and Schiller, E., Handbook on Toxicity of Inorganic Compounds, Eds. Seiler H, G., and Sigel, H.; Marcel Dekker, New York, 1988, pp. 595–617).

A process is also provided for preparing the compounds of formulas I–III. Preparation of the compounds will generally require a protecting group for the silanol or silanediol that will avoid self condensation. The protecting group must be stable and yet readily removed. Synthesis of the protected silanediol involves formation of silicon-carbon bonds using one or more types of reactions such as those which are described below, followed by deprotection to yield a silanol or silanediol through a reaction generally involving hydrolysis.

The compounds of the invention exhibit pharmaceutical activity and are therefore useful as pharmaceuticals. The compounds of formula I mimic the tetrahedral intermediate of polypeptide hydrolysis and can be incorporated into a polypeptide chain or employed alone or in combinations and used in protease enzyme inhibition. The compounds of formulas II and III are used similarly. Accordingly, a method is provided for inhibiting protease enzymes and in the treatment of related diseases.

Advantageously, the compounds of the invention provide a "cassette" which can be inserted into a target peptide or analog of that peptide to result in protease inhibition. Because the compounds are isosteres of the general obligatory tetrahedral intermediate of hydrolysis, protease inhibition using the compounds of the invention is not limited in a choice of target protease.

DETAILED DESCRIPTION OF THE INVENTION

The invention includes biologically active silanediols, exemplified by Structure II below, which are useful in the design of new drugs. The naturally occurring tetrahedral intermediate of protease mediated hydrolysis is shown in Structure I.

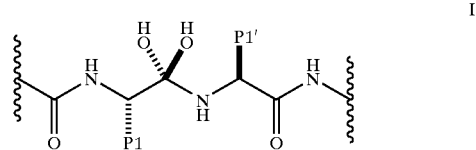

I

The Structure II mimics of the tetrahedral intermediate, e.g., when incorporated into a polypeptide chain or used alone or in combination, can be used as highly effective inhibitors of protease enzymes, particularly aspartic proteases (e.g., HIV-I protease and renin) and zinc proteases (e.g., thermolysin and carboxypeptidase A).

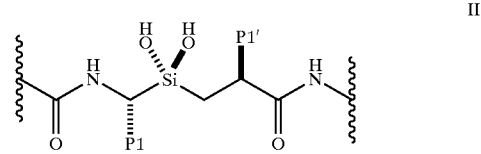

II

P1 and P1' are defined as groups on the natural substrate of a protease, or analogs of those groups, that flank the cleavage site of the substrate and are assumed to fit "subsites" on the enzyme (generally referred to as S1 and S1', respectively) that flank the active site of the enzyme. Additional sites on each side can be specified and are numbered consecutively, e.g. P2, P3, P4, . . . and P2', P3', P4', . . . etc. Schechter, I.; Berger, A. "On the Size of the Active Site in Proteases. I. Papain," Biochem. Biophys. Res. Commun. 1967, 27, 157–162. Schecter, I.; Berger, A. "On the Active Site of Proteases. III. Mapping the Active Site of Papain; Specific Peptide Inhibitors of Papain," Biochem. Biophys. Res. Commun. 1968, 32, 898–902.

The silicon-containing compounds of the invention are stable in their configuration, and in their activity. Silicon, relative to carbon, has the unique advantage of forming only stable tetrahedral gem-diol (silanediol) and not trigonal silanones. Stable carbon-based gems-diol molecules require electron withdrawing groups at the alpha position to destabilized the trigonal carbonyl and are often in equilibrium with the corresponding carbonyls. This factor and the increased acidity of the silanol as compared with the carbinol, indicates that silanol based enzyme inhibitors can hydrogen bond more strongly to an enzyme active site than carbon-based gem-diols. The term "gem" means that two identical substituents are on the same carbon or silicon, e.g., both substituents are hydroxyl groups.

Preferred compounds according to the invention include the following sites:

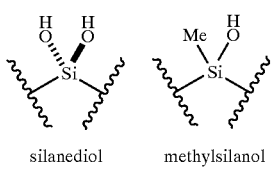

silanediol     methylsilanol

The remainder of the molecule is chosen to provide a desired or best set of properties. These properties include enzyme fit, enzyme specificity, solubility, metabolic stability, crystallinity, etc.

Non-limiting examples of compounds of the invention include the following:

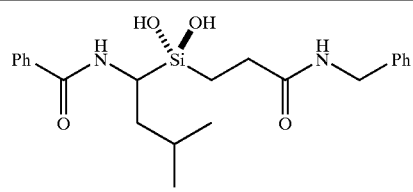

1
Benzyl 5-(benzoylamino)-4,4-dihydroxy-7-methyl-4-sila-octanamide

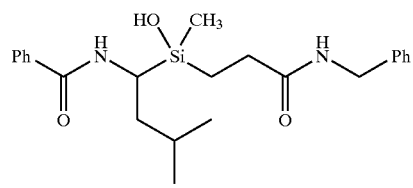

2
Benzyl 5-(benzoylamino)-4,7-dimethyl 4-hydroxy-4-sila-octanamide

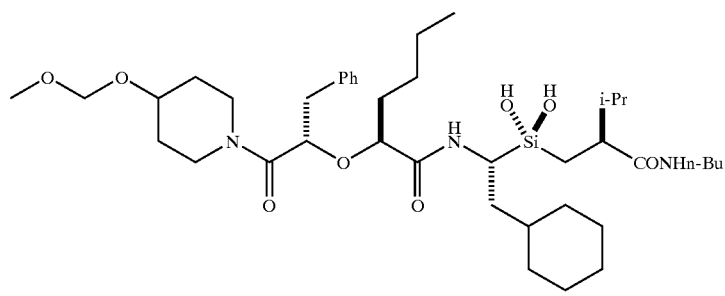

3
Butyl 6-cyclohexyl-4,4-dihydroxy-2-(S)-isopropyl-5-(S)-[2-(S)-(2-(S)-1-oxo-
1-(4-methoxymethyl-1-piperidinyl)-3-phenyl-propanoxy)-hexanoyl-
amino)]-4-sila-hexanamide

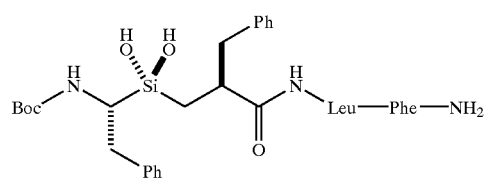

4
[5-(R)-((t-butoxycarbonyl)amino)-2-(S)-benzyl-4,4-dihydroxy-6-
phenyl-4-sila-hexanoyl]-L-leucyl]-L-phenylalanamide -continued

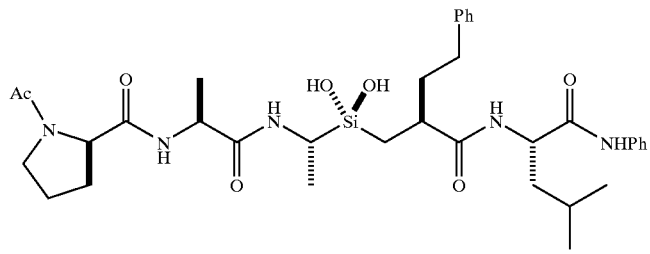

5

[[5-(R)-([Acetyl-L-prolinyl]-L-alaninyl)-amino-4,4-dihydroxy-
2-(S)-(2-phenylethyl)-4-sila-hexanoyl]-L-leucyl]-aniline

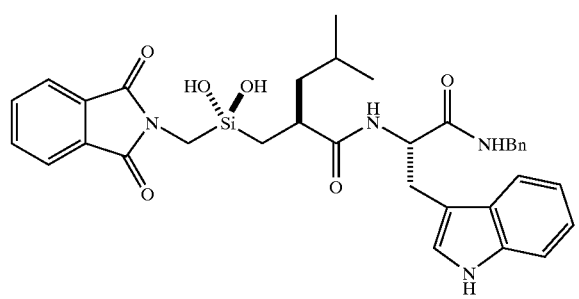

6

Benzyl[4,4-dihydroxy-2-(S)-isobutyl-5-(N-phthalamido)-4-sila-pentanoyl]-L-tryptamide

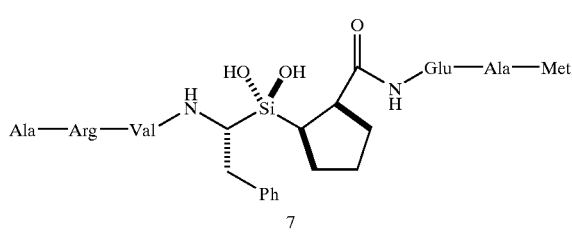

7

[[[2-(R)-[1-(R)-[[L-Alaminoyl]-L-argininoyl]-L-valinoyl]-amino]-
2-phenyl-ethyl)-dihydroxysilyl)-(R)-cyclopentane carboxy]-L-glutanoyl]-
L-alaninoyl]-L-methionine

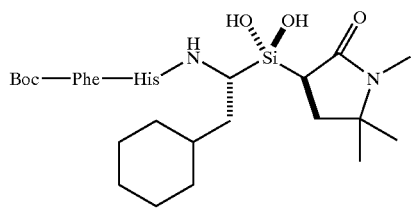

8

3-(R)-([1-((R)-[[t-Butoxycarbonyl)-L-phenyl-alanoyl]-L-histidinyl]-amino)-
2-cyclohexylethyl]-dihydroxysilyl)1,5,5-trimethyl-2-pyrrolidinone

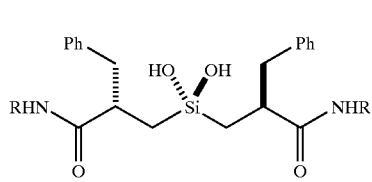

9a R = CH$_2$Ph

Di-benzyl 2-(S)-6-(S)-dibenzyl-4,4-dihydroxy-4-sila-heptanediamide

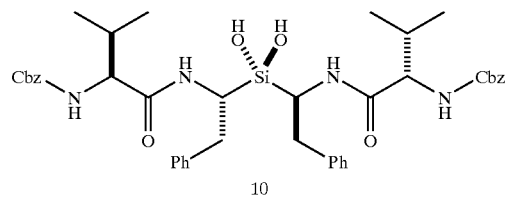

10

2-(R),4-(R)-Bis-([benzyloxycarbonyl)-L-valinyl]-amino)-3,3 dihydroxy-1,5-diphenyl-3-sila-pentane

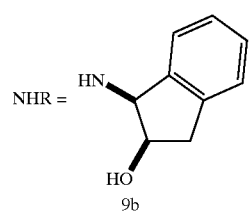

9b

Di-[1-(S)-(2,(R)-hydroxyindanyl)]2-(S)-6-(S)-dibenzyl-4,4-dihydroxy-4-sila-heptanediamide

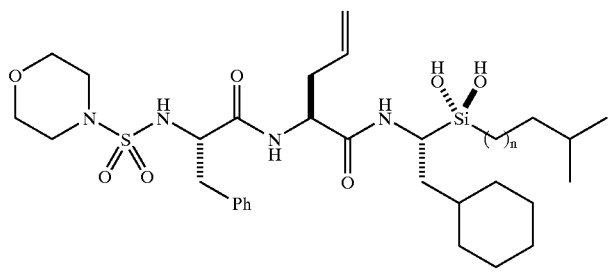

11 n = 0

[5-(R)-[[[Morpholinosulfonyl]-L-phenyl-alaninoyl]-L-allylglycinoyl]amino]-6-cyclohexyl-4,4-dihydroxy-2-methyl-4-sila-pentane 12 n = 1

[5-(R)-[[[Morpholineosulfonyl]-L-phenyl-alamino]-L-allylglycinoyl]amino]-7-cyclohexyl-5,5-dihydroxy-2-methyl-5-sila-pentane

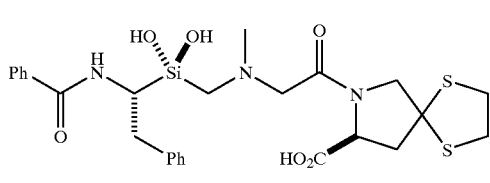

13

[[6-(R)-Benzoylamino]-3-aza 5,5-dihydroxy-3-methyl-7-phenyl-5-sila-heptanoyl]-L-4-dithianylproline

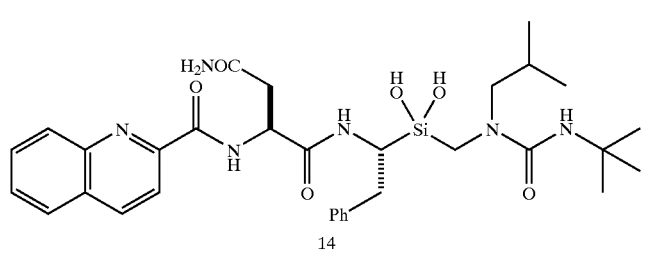

14

N-t-Butyl-N'-isobutyl-N'-[3-(R)-([[2-quinolinoyl]-L-asparinoyl]-amino)-4-phenyl-2,2-dihydroxy-2-sila-butyl]urea

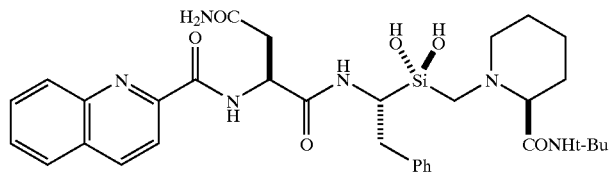

15 t-Butyl N-[3-(R)-([[2-quinolinoyl]-L-asparinoyl]-amino)-4-phenyl-2,2-dihydroxy-2-sila-butyl]-L-pipecolinamide

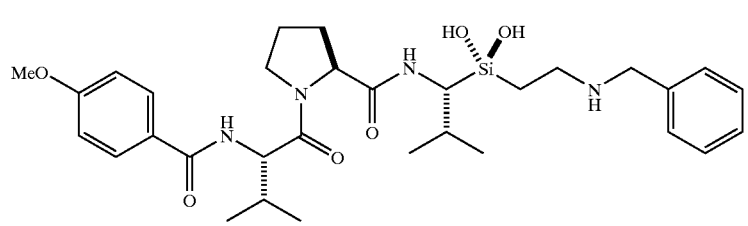

16

N-[3,3-Dihydroxy-4-(R)-([[(p-methoxy-benzoyl)-L-valinoyl]-L-prolinoyl]-amino)-5-methyl-3-sila-hexyl]benzylamine

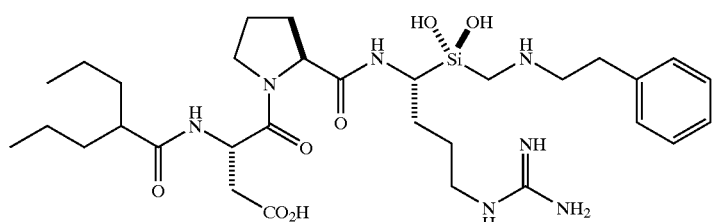

17

N-(2,2-Dihydroxy-6-guanidino-3-(R)-[[[2-n-propylpentanoyl]-L-aspartoyl]-L-prolinoyl]-amino)-2-sila-n-hexyl)N-2-phenylethyl amine

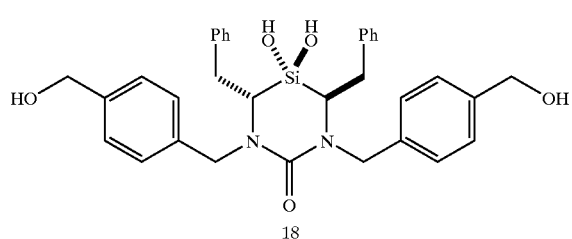

18

3,5 Bis(p-hydroxymethyl benzyl)3,5-diaza 2-(S)-6-(R)-dibenzyl-1,1-dihydroxy-1-sila-cyclohexan-4-one

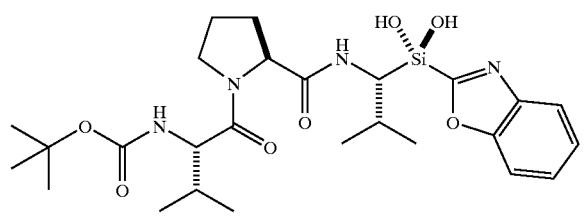

19

(1-(R)-[[i-Butoxycarbonyl)-L-valinoyl]-L-prolinoyl]-amino-2-methyl)2-benzoxaole silanediol -continued

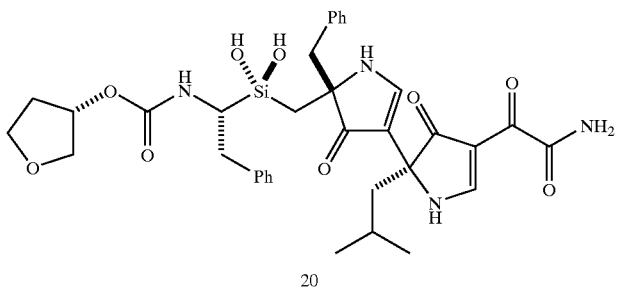

20

[1-(R)-(3-(S)-Tetrahydrofuranoxycarbonyl)-amino-2-phenylethyl]-
(3-[3-(1,2-dioxo-2-aminoethyl)-5'-isobutyl-5'-(S)-pyrrolin-4'-
one]-5-(R)-5-benzyl pyrrolin-4-one)methyl silanediol

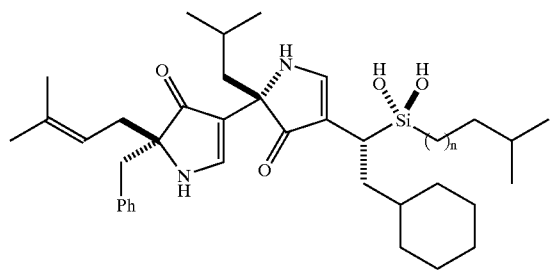

21 n = 0

6-Cyclohexyl-4,4-dihydroxy-3-(R)-[5'-(S)-5' isobutyl-5-[5"-(S)-5"-
(3-methyl-2-butenyl)-5"-benzyl 3"-pyrrolin-4" one]-3'-pyrrolin-4'-
one]-4-sila-hexane 22 n = 1

7-Cyclohexyl-5,5-dihyroxy-3-(R)-[5'-(S)-5' isobutyl-5-[5"-(S)-
5"-(3-methyl-2-butenyl)-5"-benzyl-3"-pyrrolin-4" one]-3'-
pyrrolin 4'-one]-5-sila-hexane

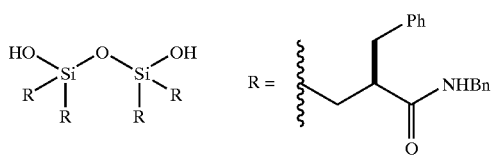

60

1,3-dihydroxy-1,1,3-3-tetra(3-[2-(S)-2-phenylmethylpropionyl])-
disiloxane tetra(N-phenylmethylamide)

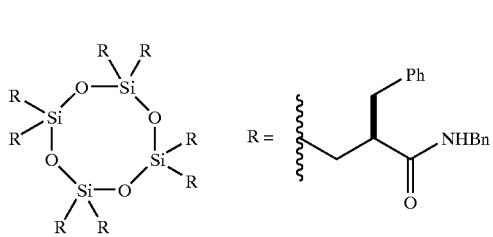

61

1,1,3,3,5,5,7,7-octa(3-[2-(S)-2-phenylmethylpropionyl)]-
cyclotetrasiloxane octa(N-phenylmethylamide)

Compounds according to formula I in which A and B are represented by a) and e) are compounds 11, 12, 16, 17 and 20. A compound according to formula I in which A and B are represented by b) and e) is compound 19. A compound according to formula I in which A and B are represented by c) and e) is compound 7. Compound 16 with

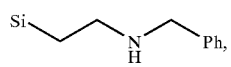

is an example of both a) and f).

Compounds according to formula I in which A and B are represented by d) and e) are compounds 1, 2, 3, 4, 5, 6 and 7. A compound according to formula I in which A and B are both represented by d) is compound 9. Compounds according to formula I in which A and B are both represented by e) are 10, 13, 14, 15, 17, 18. Compounds according to formula I in which A and B are represented by e) and f) are 8 and 16. Compounds 11, 12 and 19 also include e).

A compound according to formula II is 61. A compound according to formula III is 60.

Important considerations in the synthesis were the formation of silicon-carbon bonds, protection to avoid or control oligomerization, removal of the protecting group and hydrolysis of the silicon-containing compound to the silanol, silanediol or siloxane final product.

Since silicon-containing compounds such as silanediols have a proclivity to condense and form siloxanes or silicones, it was necessary to devise a synthesis scheme in which self condensation is inhibited during synthesis. This was achieved by protecting the diol site during synthesis. The choice of protecting group was also important because the protecting group must be capable of being removed under conditions compatible with peptide chemistry. Preferred protecting groups are ones which have unsaturation proximal to a carbon-silicon bond, for example, a phenyl which can also have additional electron donating or withdrawing groups. The protecting groups include substituted or unsubstituted phenyl, vinyl (CH=CH$_2$) and allyl (CH$_2$CH=CH$_2$).

It was determined that triflic (trifluoromethanesulfonic) acid can be used for hydrolysis of the silicon-containing compound to the silanol or silanediol final product. Other acids such as sulfuric acid, hydrofluoric acid hydrochloric acid, and acetic acid optionally in conjunction with boron trifluoride, can be used, or electrophiles other than H$^+$, such as halogens (chlorine Cl$_2$, bromine Br$_2$, iodinemonochloride ICl), or acid chlorides such as acetylchloride, or electrophiles such as mercuric chloride, can also be used.

Synthesis precursors to the compounds of the invention contain groups attached to silicon that are both generally stable and can be transformed into hydroxyl groups (silanols). These groups can be substituted or unsubstituted aryl, substituted or unsubstituted vinyl, substituted or unsubstituted allyl, substituted or unsubstituted benzyl, or a heteroatom-substituted alkyl, alkoxy or amino group. More specifically, in the synthesis precursors, Aryl includes four to ten carbons and can be substituted. Allyl includes three to ten carbons and can be substituted. Benzyl can also be substituted. Alkyl includes two to four carbons. Alkoxy includes one to four carbons. Substitutions may be by organic or inorganic groups. Inorganic substituents include double-bonded oxygen, i.e., carbonyl, or single bonded oxygen, i.e., hydroxy or alkoxy. Additional inorganic substitutents include amino, thio, halo, etc. Organic substituents include alkyl and aryl. The amines can be primary, secondary or tertiary.

The synthesis of silicon-carbon bonds can be accomplished through various reaction types.

i) As non-limiting examples, these reaction types include nucleophilic attack of a carbon nucleophile, such as a Grignard reagent, on a chlorosilane or alkoxysilane. I. Fleming "Organic Silicon Chemistry", in Comprehensive Organic Chemistry, D. Barton, W. D. Ollis. Eds, (Pergamon, N.Y., 1979), vol. 3, pp. 541–686.

For example, a nucleophilic carbon can react with a silicon attached to a leaving group:

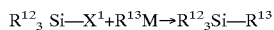

$X^1$ is preferably H, halogen, sulfonate or alkoxy

M = a metal (e.g., Li, Mg, Cu)

The $R^{12}$ groups are preferably alkyl, aryl or alkoxy.

The reactions are run in an inert solvent (e.g., ether, hexane, toluene) and under an inert atmosphere (e.g., nitrogen, argon) at a temperature between −100° C. and +150° C. Preferably the reagents are used in a 1:1 ratio, but may range from 1:10 to 10:1.

Compounds such as 1, 2 and 19 can be made using this method.

ii) Alternatively, the opposite arrangement of nucleophile and electrophile can be used, such as a nucleophilic attack by alkyldiphenylsilylcuprate on an iodoalkane.

The silicon can be the nucleophile and carbon the electrophile for example,:

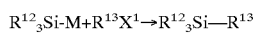

Conditions and definitions are as defined in i).

Compounds such as 11 and 12 can be made in this way.

iii) An additional method for preparing the desired organosilanes is the hydrosilylation reaction, in which a hydrogen-silicon bond is added across a carbon-carbon double bond, often catalyzed by a metal such as platinum or rhodium. I Ojima, "Hydrosilylation", in The Chemistry of Organic Silicon Compounds; S. Patai and Z. Rappoport, Eds.; Wiley: New York, 1989; Vol. 2; pp 1479–1525.

Hydrosilylation adds a silicon and hydrogen across a carbon-carbon double bond, for example:

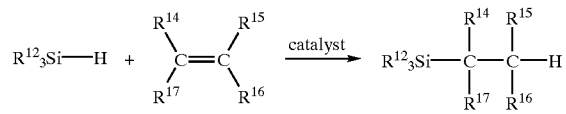

Hydrosilylation reactions are run in an inert solvent (e.g., THF, isopropanol, hexane) and at temperatures between −100° C. and +150° C. Preferably the reagents are used in a 1:1 ratio, but may range from 1:10 to 10:1. The catalyst can be a radical initiator or a metal In the case of a radical initiator, from 0.01 to 10 equivalents can be used. Examples of these catalysts are benzoyl peroxide, azo-bis-isobutyronitrile, and organoboranes in the presence of oxygen. In the case of metal catalysts, 0.0001 to 10 equivalents may be used. Various metals can be used, generally platinum or rhodium or cobalt.

Compounds such as 11 and 12 can be made in this way.

iv) Nucleophilic addition of amine (primary or secondary) to alkenylsilanes, usually with base catalysis, can be used, for example:

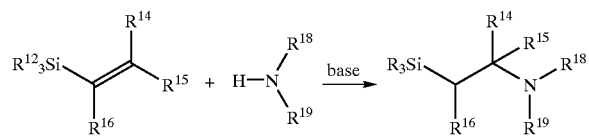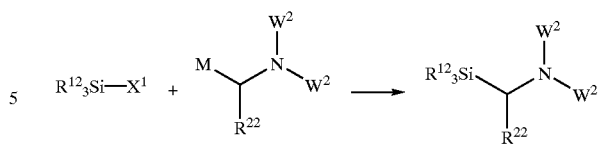

$R^{14}$ through $R^{19}$ are independently chosen groups, preferably H, or optionally substituted alkyl or aryl. The base is preferably an organometallic reagent such as a Grignard reagent or n-butyllithium and is used in a catalytic amount (0.5 to 0.01 equivalents). One equivalent of the amine is preferably used, but can be used in excess. An inert solvent may be used (ether, hexane).

Compounds such as 16 can be made in this way.

v) Nucleophilic displacement of a halogen by an amine nucleophile can be used, for example:

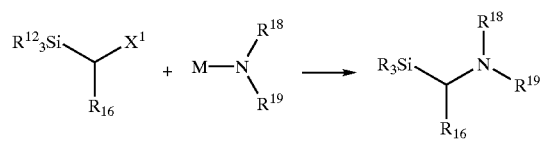

$X^1$ is preferably halogen or sulfonate. M is preferably H or a metal (e.g., Li, Na, K, Mg). The moiety $NR^{18}R^{19}$ is preferably $N_3$ (azide) or phthalimide or succinimide, or $R^{18}$ and $R^{19}$ can be H, optionally substituted alkyl or optionally substituted aryl. Preferably a polar, inert solvent is used e.g., alcohol, ether DMSO, DMF, THF). The temperature is generally between −50° C. and +150° C. At least one equivalent of $NR^{18}R^{19}$ is used, but excess may be employed. When azide is used for $NR^{18}R^{19}$ the result azide product is reduced to an amine using standard conditions, including but not limited to hydrogenation (e.g., hydrogen gas, platinum catalyst), treatment with thiols, or treatment with lithium aluminum hydride.

Compounds such as 1 and 2 can be made in this way.

vi) Hydrosilylation of an enamine derivative can be used, for example:

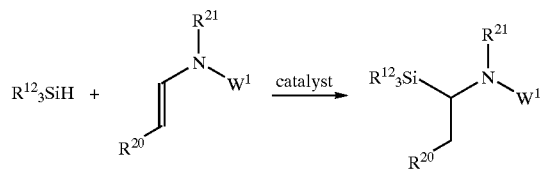

$R^{20}$ and $R^{21}$ are preferably H, optionally substituted alkyl or optionally substituted aryl. $W^1$ is preferable a substituted carbonyl derivative such that N—$W^1$ constitutes an amide, carbamate, or urea. The catalyst is preferably a rhodium derivative such as dirhodium tetraacetate. Preferably the silane and the enamine derivative are used in a ratio of 1:1. Preferably between 0.5 and 0.0001 equivalents of the catalyst is used. The temperature of the reaction is between −50° C. and +150° C. A reference for this chemistry: Murai, T.; Oda, T.; Kimura, F.; Onishi, H.; Kanda, T.; Kato, S. "Rhodium(II) acetate Catalysed Hydrosilylation of Enamides and N-Vinylureas leading to 1-(Trialkylsilyl) alkylamine Derivatives," J. Chem. Soc., Chem. Commun 2143–2144 (1994).

Compounds such as 3 and 8 can be made in this way.

vii) Silylation of an alpha-metallo amine derivative can be used, for example:

$W^2$ groups are independently chosen and are preferably a metalation directing group (MDG) or an optionally substituted alkyl or an optionally substituted aryl. $R^{22}$ and one of the $W^2$ groups can form a ring or both of the $W^2$ groups can form a ring. MDGs are preferably substituted carbonyl groups or substituted imine group or a sulfonyl group or a phosphoryl group. P. Beak, W. J. Zajdel, D. B. Reitz, "Metalation and Electrophilic Substitution of Amine Derivatives Adjacent to Nitrogen: α-Metallo Amine Synthetic Equivalents," Chem. Rev. 84, 471–523 (1984). M is a metal, preferably Li, Na, Mg, or Sn. The temperature of the reaction is preferably between −100° C. and +50° C.

Compounds such as 10, 13 and 18 can be made in this way.

viii) Rearrangement of alpha-metallo N-silyl compounds can be used, for example:

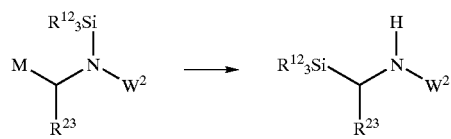

$W^2$ group is preferably a metalation directing group (MDG, as defined in (vii), above) or an optionally substituted alkyl or an optionally substituted aryl. M is a metal, preferably Li, Na, Mg, or Sn. The temperature of the reaction is preferably between −100° C. and +50° C.

Compounds such as 16 and 17 can be made in this way.

Deprotection of the silanol or silanediol generally involves hydrolysis. In the case of phenyltrialkyl or diphenyldialkylsilanes, this is accomplished by treatment with acid to break the silicon-phenyl bond, followed by addition of water to generate the silanol or silanediol. Eaborn, E. "Cleavages of Aryl-Silicon and Related Bonds by Electrophies," J. Organomet. Chem. 100, 43–57 (1975).

In synthesis methods i) through viii), $R^{12}$–$R^{23}$ can be chosen to provide A, B and/or $R^1$–$R^{11}$ in the final product. With $R^{12}$, a further reaction sequence results in X and/or Y in the final product. $W^1$ and $W^2$ will generally be removed. All of the precursor compounds in i)–viii) can be made by methods known in the art or the reagents are commercially available. An example of a synthesis scheme is as follows:

Scheme 1

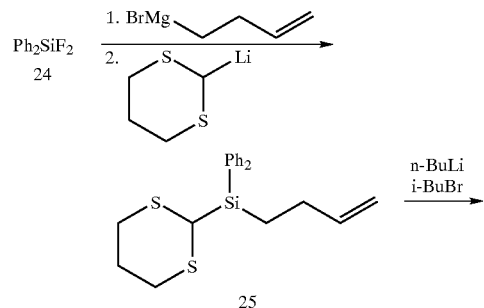

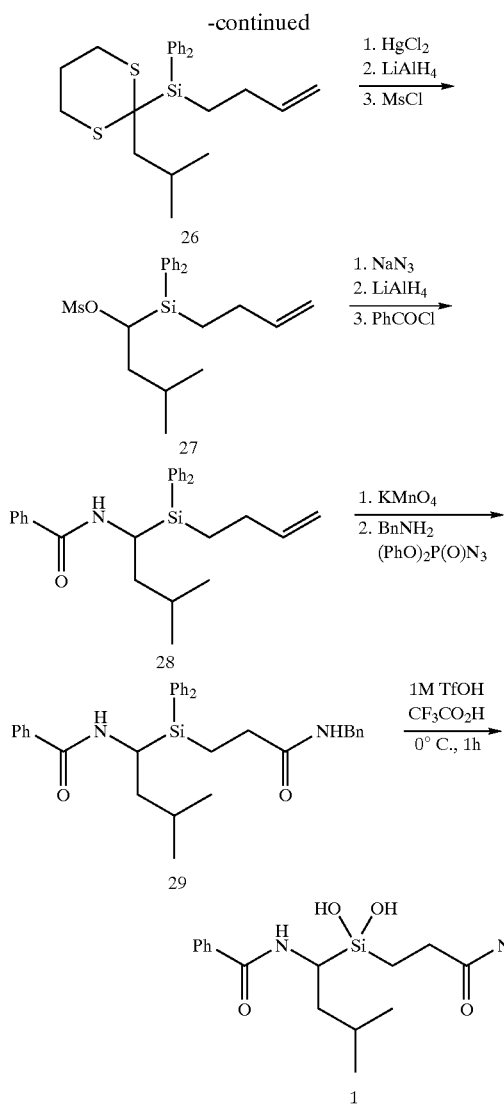

Difluorodiphenylsilane 24 is alkylated sequentially with 1-bromomagnesium-3-butene and 2-lithio-1,3-dithiane to give 25. Deprotonation of the dithiane 25 with n-butyllithium and alkylation of the resulting anion gives 26. Hydrolysis of dithiane 26 with mercury(II) chloride yields a silaketone which is then reduced with lithium aluminum hydride. The resulting alcohol is derivatized with methanesulfonyl chloride to give the methylsulfonate 27. This sulfonate is then displaced with sodium azide to give an alpha-azido silane that is reduced to an alpha-amino silane with lithium aluminum hydride. The amine is condensed with benzoyl chloride to yield amide 28. Oxidative cleavage of the alkene in 28 to a carboxylic acid is performed with potassium permanganate. The acid is then condensed with benzyl amine using diphenylphosphoryl azide as a dehydrating agent. The resulting diamide 29 is treated with trifluoromethanesulfonic acid in trifluoroacetic acid at 0° C. for one hour. Addition of water and extraction of the aqueous phase with dichloromethane yields silanediol 1.

The compounds of the invention inhibit protease enzymes including metallo, apartyl and serine proteases.

Four classes of proteases are known and these are categorized by the catalytic functionality at the active site: aspartic proteases, metalloproteases, serine proteases and cysteine proteases. All four classes contain important therapeutic targets for enzyme inhibition.

Non-limiting examples of therapeutic targets are shown in the table below.

TABLE 1

| Protease Class | Example | Pathology |
|---|---|---|
| Aspartic Protease | Renin | Hypertension |
|  | HIV-1 protease | AIDS |
| Metalloprotease | Angiotensin-converting enzyme | Hypertension |
|  | Collagenase | Arthritis |
|  | Enkephalinases | Analgesia |
|  | Stromelysin | Arthritis |
|  | Endothelin Converting Enzyme | Renal Failure |
|  | Neutral Endopeptidase | Hypertension |
| Serine Protease | Plasmin, Plasminogen Activator | Cell invasion |
|  | Elastases, cathepsin G | Emphysema, cystic fibrosis, arthritis |
|  | Mast-cell proteases | Hypertension |
|  | Prolyl endopeptidase | Infertility, anaphylaxis |
|  | Thrombin | Thrombosis |
|  | Factor Xa | Thrombosis |
| Cysteine Protease | Picornavirus protease | Viral Diseases |
|  | Cathepsins | Muscular dystrophy |

As non-limiting examples, compounds 1, 2 and 13 depicted above can be used to inhibit angiontensin-converting enzyme in the treatment of hypertension. Compounds 3, 8, 11, 12, 21 and 22 can be used to inhibit renin in the treatment of hypertension. Compounds 4, 7, 9, 10, 14, 15, 18 and 20 can be used to inhibit HIV protease in the treatment of AIDS. Compounds 16 and 19 can be used to inhibit elastase in the treatment of emphysema and cystic fibrosis. Compound 17 can be used to inhibit thrombin in the treatment of thrombosis. Compound 5 can be used to inhibit stromelysin in the treatment of arthritis. Compound 6 can be used to inhibit collagenase in the treatment of arthritis.

The naturally-occurring polypeptide cleavage mechanisms of action of the four classes of proteases have been studied.

Aspartic and metallo proteases catalyze the addition of water to the amide bond and stabilize the tetrahedral intermediate of hydrolysis by hydrogen bonding to a pair of aspartic acid residues in aspartic proteases or by coordination to a metal (usually zinc) in metallo proteases.

With aspartic proteases, the catalytic mechanism involves the concerted action of two aspartyl carboxy groups, only one of which is protonated. De Voss, J. J. et al., J. Med. Chem 37, 665–673 (1994). The protonated aspartyl hydrogen bonds to the amide carbonyl of the substrate and the unprotonated aspartyl to a water molecule. Transfer of the hydrogen from the aspartyl to the carbonyl group of the substrate coupled with addition of a water molecule gives a gem-diol transition-state intermediate. One of the two hydrogens of the water is retained and shared by the aspartyl groups. The tetrahedral gem-diol intermediate is then cleaved, again with the help of the two differently protonated aspartyl groups, inhibitors of aspartic acid proteases such as renin and HIV-1, have included hydroxyethylene, dihydroxyethylene, α-dicarbonyl, hydroxyethylamine, phosphinate, reduced amide and statine-like groups. Vacca, J. P., "Design of Tight-Binding Human Immunodeficiency Virus Type 1 Protease Inhibitors", Methods Enzymol. 241, 311–334 (1994). But there has been no suggestion to use silanols to inhibit aspartic proteases.

The silanol-containing compounds of the invention are isosteres of the hydrated amide bonds that aspartic proteases act upon, but, advantageously, the compounds of the invention are not cleavable under enzymatic conditions. The silanols are tetrahedral in structure and are believed to bind to the aspartic protease enzyme by forming hydrogen bonds to the aspartic acid residues that are present in the enzyme active site. Thus these isosteres function as stable, non-hydrolyzable transition-state mimics (analogs) of the enzyme-catalyzed hydrolysis reaction of the substrate amide bond.

In metalloproteases, a metal coordinates and activates the polypeptide amide carbonyl for nucleophilic attack by water. Carboxypeptidase A and thermolysin are two well studied metalloproteases. Matthews, B. W., Acc. Chem, Res. 21, 333 (1988); Christianson, D. W. and Lipscomb, W. N., Acc. Chem. Res. 22, 62 (1989). Both of these contain zinc at the active site, similar to the clinically important angiotensin-converting enzyme (ACE) (Rich, D. H., "Peptidase Inhibitors," in Comprehensive Medicinal Chemistry, C. Hansch et al., Ed., Pergamon, N.Y., 1990, pp. 391–441) and enkephanlinase enzymes. Other metalloproteases are Endothelin Converting Enzyme (ECE), the matrix metalloproteases (collagenase, stromelysin, gelatinase) and neural endopeptidase.

Inhibitors of metalloproteases have included sites incorporating thiols, aldehydes which can hydrate, hydroxamic acid, carboxylalkylamine, ketone (which can hydrate), phosphinic acid, phosphonamide, phosphonate and aminoketone (which can hydrate). For example, an inhibitor of ACE includes a ketone site (Gordon, E. M. et al., "Ketomethyl-dipeptides II. Effect of Modification of the α-Aminoketone Portion on Inhibition of Angiotensin Converting Enzyme", Biochem. Biophys. Res. Commun. 124, 148–155 (1984)) which is expected to be hydrated as the gem-diol. There has been no suggestion to utilize silanols in the inhibition of metalloproteases.

Serine and cysteine proteases utilize a two-step process with an initial nucleophilic attack on an amide carbonyl by a serine or cysteine residue, generating a tetrahedral intermediate of hydrolysis which is covalently attached to the enzyme. These mechanisms of hydrolysis are discussed in detail by R. H. Rich, "Peptidase Inhibitors" in Comprehensive Medicinal Chemistry, P. G. Sommes and J. B. Taylor, eds., Pergamon, N.Y. 1990, Vol. 2, pp. 391–441, and G. Fischer, "Trends in Protease Inhibition". National Product Reports, 1988, 465–495. There has been no suggestion to utilize silanols in the inhibition of serine proteases or cysteine proteases.

Serine proteases include, for example, thrombin and elastase. The mode of action of serine proteases involves the amino acid serine whose alcohol acts as a nucleophile. Inhibitors of serine protease include sites incorporating trifluoromethylketone, aldehyde, boronic acid, α-dicarbonyl, fluoromethylene ketone, borinic acid and phosphonate. In addition, alkylating agents can permanently derivatize the serine nucleophile at the enzyme active site. Activated carbonyls or other electrophilic centers interact with the nuclephilic serine oxygen forming a covalent, but not necessarily permanently bound, complex. More specifically, the serine protease, α-lytic protease is inhibited by a peptide compound containing phenyl phosphonate ester

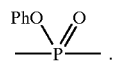

Bone, R. et al., "Crystal Structures of α-Lytic Protease Complexes with Irreversibly Bound Phosphonate Esters", Biochemistry 30, 2263–2272 (1991). As another example, carbon-based 1,1-diols, such as hydrated trifluoromethylketones also inhibit serine protease (Govardhan, C. P. and Abeles, R. H., "Structure-Activity Studies of Fluoroketone Inhibitors of α-Lytic Protease and Human Leucocyte Elastase", Arch. Biochem. Biophys. 280, 137–146 (1990)). Beginning with

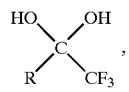

the inhibitor is dehydrated to the ketone which then reacts with the serine alcohol nucleophile. In the invention, in the inhibition of serine protease enzymes, the oxygens on silicon are exchangeable with the serine alcohol nucleophile. Studies of silane stereochemistry provide convincing evidence for the nucleophilic displacement of oxygen substituents on silicon by alcohols (Corriu, R. J. P. et al., "Stereochemistry at Silicon", Topics in Stereochemistry 15, 80–103 (1984)).

In the silicon-containing protease inhibitors of the invention, the carbon-silicon bond is strong and non-hydrolyzable, and the silicon is tetrahedral. Hydroxyl Groups on silicon are good hydrogen bond acceptors and are also slightly more acidic than carbinols, making them excellent hydrogen bond donors. They will therefore hydrogen bond to aspartic acid groups in aspartic proteases and will also act as a chelating group for the metal of metalloproteases. In addition, the hydroxyl groups on silicon are exchangeable with water and will therefore exchange with a serine hydroxyl for serine protease inhibition.

The compounds of the invention are particularly effective, for example, in the inhibition of aspartic proteases HIV-1 protease and renin; metalloproteases ACE, collagenase and stromelysin; and serine proteases thrombin and elastin.

The amount of compound used for inhibition can be determined analogously with known inhibitors of enzymes such as renin or other enzymes listed in TABLE 1 above. Accordingly, the compounds can be used in the treatment of the pathologic conditions such as those listed in TABLE 1. The compounds exhibit antiretroviral activity an can be used to treat retroviral disease such as human immunodeficiency syndrome (AIDS) analogously with the known inhibitors described by Fisher, et al. (Fisher, J. F.; Tarpley, W. G.; Thaisrivongs, S. "HIV Protease Inhibitors," in Design of Enzyme Inhibitors as Drugs; M. Sandler and H. J. Smith, Ed.; Oxford University: New York, 1994; Vol. 2; pp 226–289).

For the pharmaceutical purposes described above, the compounds of the invention can be formulated per se in pharmaceutical preparations or formulated in the form of pharmaceutically acceptable salts, optionally with known pharmaceutically acceptable adjuvants or carriers. These preparations can be prepared according to conventional chemical methods and can be administered enterally, e.g., orally as tablets; parentally, e.g., intravenously intramuscularly or subcutaneously, as injectable solutions or suspensions; or in the form of a spray inhalation.

Pharmaceutical preparations contain a protease-inhibiting effective amount of the compound of formula I, II and/or III. The dosage, analogously with known enzyme inhibiting peptides, depends on the species, body weight, age and mode of administration. The daily dosage is preferably about 0.02–500 mg/kg of body weight per day, more preferably, about 1–20 mg/kg.

EXAMPLES

The invention will be illustrated by the following non-limiting examples. Various abbreviations are used in the examples.

| Abbreviations | |
|---|---|
| br | broad |
| Bu | butyl |
| t-Bu | tert-butyl |
| i-Bu | iso-butyl |
| calcd | calculated |
| chloramine-T | N-chloro-p-toluenesulfonamide, sodium salt |
| CI | chemical ionization |
| d | doublet |
| DCC | dicyclohexylcarbodiimide |
| dd | doublet of doublets |
| DEC | 1-(3-dimethylaminopropyl)-3-ethylcarbodiimide hydrochloride |
| DMF | dimethylformamide |
| DPPA | diphenylphosphoryl azide |
| EI | electron ionization |
| Et | ethyl |
| eq | equivalent |
| FAB | fast atom bombardment |
| FTIR | fourier transform infrared spectroscopy |
| h | hour(s) |
| HOBT | 1-hydroxybenzotriazole |
| HPLC | high performance liquid chromatography |
| HRMS | high resolution mass spectroscopy |
| Hz | hertz |
| IR | infrared |
| M | molar |
| m/e | mass to charge ratio |
| m | multiplet |
| M+ | parent ion peak (mass spectrum) |
| MHz | megahertz |
| Ms | methanesulfonyl (mesyl) |
| Me | methyl |
| min | minute(s) |
| mp | melting point |
| MS | mass spectrometry |
| NMR | nuclear magnetic resonance |
| pd | pair of doublets |
| Ph | phenyl |
| i-pr | iso-propyl |
| q | quartet |
| $R_f$ | retention factor |
| rt | room temperature |
| s | singlet |
| sat | saturated |
| sm | starting material |
| t | triplet |
| tert | tertiary |
| Tf | trifluoromethanesulfonyl (triflyl) |
| 2TFA | trifluoroacetic acid |
| TfOH | trifluoromethanesulfonic (triflic) acid |
| THF | tetrahydrofuran |
| TLC | thin layer chromatography |
| TMS | trimethylsilyl |
| Ts | para-toluenesulfonyl (tosyl) |
| UV | ultraviolet |

The synthesis of α-silyl alcohol 34 is shown in the scheme below.

Scheme 2
Synthesis of α-Silyl Alcohol 34

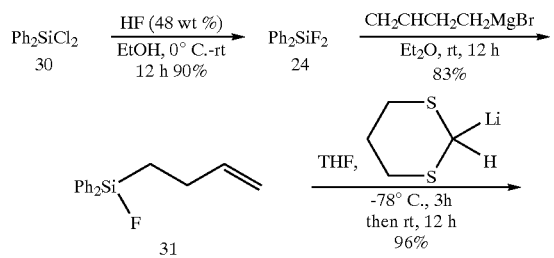

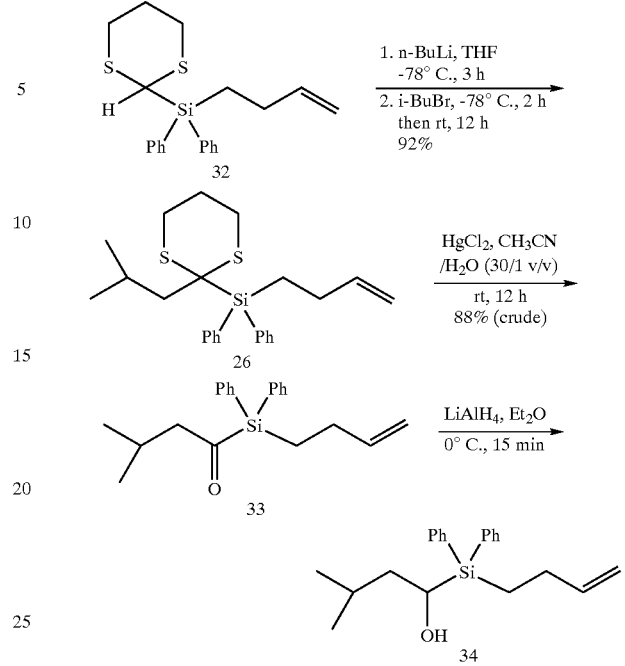

The α-silyl alcohol can be used as an intermediate in the production of silanediols.

Difluorodiphenylsilane (24). To a solution of dichlorosilane 14 (20 g, 79 mmol) in ethanol (200 mL) at 0° C. was added dropwise over 10 min hydrofluoric acid (48 wt % in water, 20 mL), and the mixture was allowed to warm to rt. After stirring overnight, the reaction mixture was poured into water (500 mL). The colorless oil that settled on the bottom was isolated and distilled (95° C., 20 mm Hg) to provide pure 24 (15.7 g, 90%): $^1$H NMR (300 MHz, CDCl$_3$) δ 7.74 (d, J=6.8 Hz, 4H), 7.60–7.56 (m, 2H), 7.50–7.45 (m, 4H); $^{13}$C NMR (75 MHz, CDCl$_3$) δ 134.8, 132.4, 128.6, 128.2.

(3-Buten-1-yl)diphenylfluorosilane (31). In a two-neck flask equipped with a condenser was placed magnesium (3.46 g, 142 mmol) and a crystal of iodine. The flask was warmed with heat gun until iodine had sublimed. A solution of 4-bromo-1-butene (9.62 g, 71.3 mmol) in ether (100 mL) was added dropwise in 30 min and the resulting mixture refluxed for 2 h. This Grignard solution was cooled to rt and added over 30 min via cannula to a second flask containing 24 (15.7 g, 71.3 mmol) in ether (100 mL) at rt. After stirring overnight at rt under argon, the reaction mixture was quenched with water (20 mL) and the organic layer isolated. The aqueous layer was extracted twice with 50-mL portions of ether. The combined organic extracts were washed with saturated aqueous NaCl, dried over Na$_2$SO$_4$, and concentrated. Distillation (134° C., 1.5 mm Hg) provided pure 31 as a colorless oil (15.2 g, 83%): $^1$H NMR (300 MHz, CDCl$_3$) δ 7.62 (d, J=7.8 Hz, 4H), 7.50–7.39 (m, 6H), 5.97–5.83 (m, 1H), 5.02 (dd, J=17.1, 1.7 Hz, 1H), 4.94 (dd, J=10.2, 1.7 Hz, IH), 2.28–2.20 (m, 2H), 1.38–1.30 (m, 2H); $^{13}$C NMR (75 MHz, CDCl$_3$) δ140.9, 135.9, 134.1, 129.7, 127.8, 113.1, 26.9, 14.0.

(3-Buten-1-yl)(1,3-dithian-2-yl)diphenylsilane (32). To a solution of 1,3-dithiane (6.77 g, 56.3 mmol) in THF (120 mL) at −78° C. was added dropwise over 10 min n-butyllithium (1.6 M in hexane, 50 mmol), and the solution was stirred for 2 h under argon. A solution of 31 (11.1 g, 43.3 mmol) in THF (100 mL) was added, the mixture was stirred for 3 h at −78° C., and overnight at rt. The reaction mixture was quenched with water (100 mL) and the organic layer isolated. The aqueous layer was extracted with two 100-mL portions of ethyl ether. The combined organic extracts were washed with saturated aqueous NaCl, dried over $Na_2SO_4$, and concentrated. Flash chromatography over silica gel (1/9EtOAc:hexane) gave 32 contaminated with 1,3-dithiane. The latter was removed by sublimation (54° C., 8.0 mm Hg). Recrystallization from $Et_2O$ provided pure 32 as a colorless solid (14.8 g, 96%): $R_f$=0.40 (1/49 EtOAc:hexane); mp 47–49° C.; $^1$H NMR (300 MHz, $CDCl_3$) δ 7.66 (d, J=7.8 Hz, 4H), 7.43 (m, 6H), 5.90 (m, 1H), 5.02 (dd, J=17.1, 1.7 Hz 1H), 4.91 (dd, J=10.2, 1.7 Hz, 1H), 4.26 (s, 1H), 2.92 (t, J=11.8 Hz, 2H), 2.71 (m, 2H), 2.19 (m, 2H), 2.07 (m, 2H), 1.37 (m, 2H); $^{13}$C NMR (75 MHz, $CDCl_3$)δ 141.1, 135.9, 132.4, 130.2, 128.0, 113.2, 32.3, 31.5, 27.5, 25.8, 10.5; IR (film) 3068 (m), 3047 (m), 2897 (s), 2840 (m), 1961 (w), 1890 (w), 1826 (w), 1639 (m), 1490 (w), 1429 (s), 1275 (m), 1112 (s), 1003 (m), 911 (s), 785 (m), 744(s), 703 (s) cm$^{-1}$; MS (FAB) m/e (rel. intensity) 357 (MH$^+$, 11), 356 (11), 355 (25), 301 (18), 279 (13), 237 (36), 227 (11), 225 (18), 221 (14), 215 (14), 213 (18), 212 (12), 211 (100), 209 (9), 207 (15); HRMS (FAB) calcd for $C_{20}H_{23}S_2Si$: 355.1010 (MH$^+$−2). found: 355. 1020. Anal. Calcd for $C_{20}H_{24}S_2Si$: C, 67.36; H, 6.78. Found: C, 67.08; H, 6.78.

(3-Buten-1-yl)[2-(2-methyl-1-propyl)-1,3-dithian-2-yl] diphenylsilane (26). To a solution of 32 (4.68 g, 13.1 mmol) in THF (100 mL) at −78° C. was added dropwise over 10 min n-butyllithium (1.6 M in hexanes, 18.4 mmol). After 3 h of stirring under argon, 1-bromo-2-methylpropane (2.14 mL, 19.7 mmol) was added dropwise over 5 min, and the mixture was stirred for 2 h at −78° C. and overnight at rt. The reaction mixture was quenched with water (10 mL) and the excess organic solvent was removed under reduced pressure. The crude mixture was extracted with three 100-mL portions of EtOAc. The combined organic extracts were washed with saturated aqueous NaCl, dried over $Na_2SO_4$, and concentrated. Flash chromatography over silica gel (1/9 EtOAc:hexane) gave pure 26 as a colorless solid (5.0 g, 92%): $R_f$=0.75 (1/9 EtOAc:hexane); mp 67–69° C.; $^1$H NMR (300 MHz, $CDCl_3$) δ 7.83 (d, J=6.0 Hz, 4H), 7.40 (m, 6H), 5.88 (m, 1H), 4.97 (dd, J=17.1, 1.7 Hz, 1H), 4.88 (dd, J=10.1, 1.7 Hz, 1H), 3.04 (m, 2H), 2.49 (t, J=4.3 Hz 1H), 2.44 (t, J=4.1 Hz, 1H), 2.08 (d, J=5.1 Hz, 2H), 1.98 (m, 4H), 1.79 (m, 1H), 1.54 (m, 2H), 0.82 (d, J=6.7 Hz, 6H); $^{13}$C NMR (75 MHz, $CDCl_3$)δ 141.5, 136.7, 132.9, 129.9, 127.7, 113.0, 45.7, 39.9, 28.3, 27.2, 24.6, 24.3, 24.2, 11.0; IR (film) 3068 (m), 3043 (m), 2951 (s), 2912 (s), 2863 (m), 1432 (s), 1274 (w), 1113 (s), 997 (m), 913 (m), 738 (s), 705 (s) cm$^{-1}$; MS (EI) m/e (rel. intensity) 289 (M$^+$−123, 3), 237 (8), 183 (72), 175 (100), 159 (32), 143 (17), 119 (16), 105 (35); HRMS (FAB) calcd for $C_{24}H_{32}S_2Si$: 412.1715 (ME+−1). found: 412.1727. Anal. Calcd for $C_{24}H_{32}S_2Si$: C, 69.84; H, 7.82. Found: C, 70.08; H, 8.07.

1-[(3-Buten-1-yl)diphenylsilyl]-3-methyl-1-butanone (33). To a solution of 26 (4.64 g 11.2 mmol) in $CH_3CN$ (300 mL) was added water (10 mL) and $HgCl_2$ (15.26 g, 56.21 mmol). After stirring overnight at rt, the mixture was concentrated and partitioned between water (100 mL) and hexane (200 mL). The organic layer was isolated and the aqueous layer extracted with hexane (50 mL). The combined organic extracts were washed with saturated aqueous NaCl and dried over $Na_2SO_4$. Concentration to dryness in vacuo at rt gave crude ketone 33 as a yellow oil (3.2 g, 88%): $R_f$=0.80 (1/9 EtOAc:hexane); $^1$H NMR (300 MHz, $CDCl_3$) δ 7.58 (d, J=6.4 Hz, 4H), 7.44 (m, 6H), 5.88 (m, 1H), 4.99 (dd, J=17.1, 1.6 Hz, 1H), 4.91 (dd, J=10.2, 1.6 Hz, 1H), 2.50 (d, J=6.6 Hz, 2H), 2.14 (m, 2H), 1.36 (m, 2H), 0.95 (m, 1H), 0.76 (d, J=6.7 Hz, 6H); IR (neat) 3068 (m), 3046(m), 2956(s), 2925 (m), 2864 (m), 1956 (w), 1886 (w), 1826(w), 1641 (s), 1471 (m), 1431 (s), 1113 (s), 1000 (m), 910 (m), 743 (s), 702 (s) cm$^{-1}$; MS (FAB) m/e (rel. intensity) 323 (MH+, 15), 322 (24), 321 (89), 267, (17), 236 (36), 198 (20), 182 (63), 169 (100), 167 (15), 159 (31); HRMS (FAB) calcd for $C_{21}H_{25}OSi$: 321.1675 (MH$^+$−2). found: 321.1670.

1-[(3-Buten-1-yl)diphenylsilyl]-3-methyl-1-butanol (34). To a solution of 33 (3.0 g, 9.3 mmol) in ethyl ether (100 mL) at 0° C. was added lithium aluminum hydride (1.0 M in ethyl ether, 47 mmol). After stirring for 15 min at 0° C. under argon, the reaction mixture was diluted with ethyl ether (300 mL) and quenched with saturated aqueous $Na_2SO_4$ until evolution of hydrogen had ceased. The mixture was dried with solid $Na_2SO_4$ and filtered, and the residue was extracted with ether (50 mL). The organic extracts were combined and concentrated in vacuo. Flash chromatography over silica gel (1/9 EtOAc:hexane) gave pure 34 as a colorless oil (2.1 g, 69%): $R_f$=0.60 (1/9 EtOAc:hexane); $^1$H NMR (300 MHz, $CDCl_3$) δ 7.57 (m, 4H), 7.37 (m, 6H), 5.87 (m, 1H), 4.97 (dd, J=17.1, 1.7 Hz, 1H), 4.88 (dd, J=102, 1.7 Hz, 1H), 4.08 (d, J=12.1 Hz, 1H), 2.12 (m, 2H), 1.85 (m, 1H), 1.58 (m, 1H), 1.26 (m, 4H), 0.88 (d, J=6.2 Hz, 6H); $^{13}$C NMR (75 MHz $CDCl_3$) δ 141.4, 135.7, 133.8, 129.8, 128.2, 113.3, 61.5, 42.4, 27.5, 24.2, 23.7, 20.7, 9.8; IR (neat) 3565 (m), 3452 (m, br), 3069 (m), 3050 (m), 2955 (s), 2910 (s), 2869 (m), 1965 (w), 1894 (w), 1832 (w), 1642 (m), 1469 (m), 1434 (s), 1369 (w), 1116 (s), 1001 m), 916 (m), 743 (s), 705 (s) cm$^{-1}$; MS (FAB) m/e (rel. intensity) 323 (MH$^+$−2, 5), 269 (21), 238 (11), 198 (57), 1.83 (100), 181 (10), 177 (23), 161 (14), 159 (56), 123 (15), 99 (12); HRMS (FAB) calcd for $C_{21}H_{27}OSi$: 323.1831 (MH$^+$−2). found: 323.1824. Anal. Calcd for $C_{21}H_{28}SiO$: C, 77.72; H, 8.70. Found: C, 77.60; H, 8.67.

The synthesis of a dipeptide mimic 29 beginning with α-silyl alcohol 34 is shown in the scheme below.

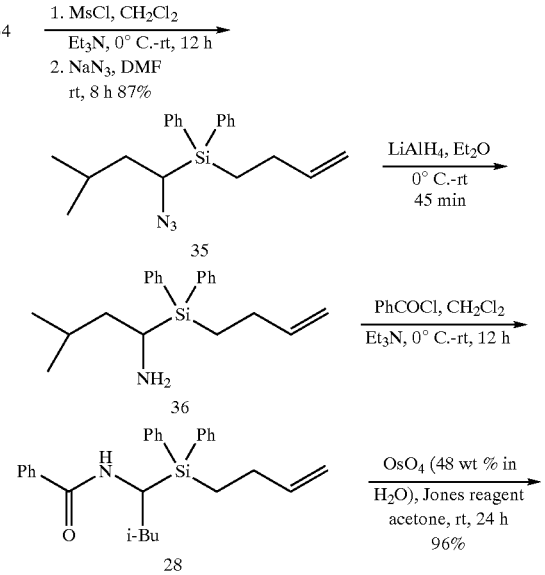

Scheme 3
Synthesis of Dipeptide Mimic 29

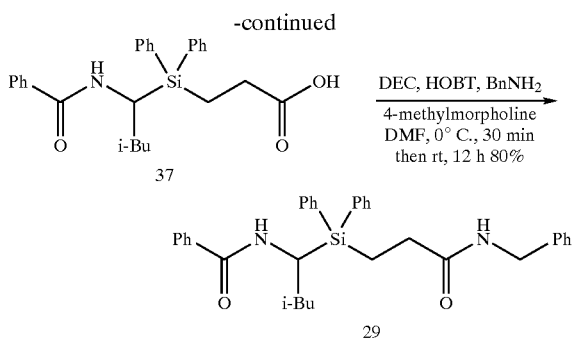

(1-Azido-3-methylbutyl)(3-Buten-1-yl)diphenylsilane (35). To a solution of 34 (1.68 g, 5.16 mmol) in CH$_2$Cl$_2$ (100 mL) and Et$_3$N (3.6 mL) at 0° C. was added dropwise over 5 min methanesulfonyl chloride (2.96 g, 25.8 mmol), and the solution was allowed to warm to rt over 1 h. After stirring overnight under argon, the mixture was cooled to 0° C. and quenched with water (50 mL). The organic layer was isolated and the aqueous layer extracted twice with 20-mL portions of CH$_2$Cl$_2$. The combined organic extracts were concentrated in vacuo at rt. The crude mesylate was dissolved in DMF (100 mL), and to this solution was added sodium azide (1.68 g, 25.8 mmol). After stirring for 8 h at rt, the mixture was partitioned between water (200 mL) and EtOAc (200 mL). The organic layer was isolated and aqueous layer extracted twice with 50-mL portions of EtOAc. The combined organic exctacts were washed with saturated aqueous NaCl, dried over Na$_2$SO$_4$, and concentrated. Flash chromatography over silica gel (1/9 EtOAc:hexane) gave pure 35 as a colorless oil (1.57 g, 87%): R$_f$=0.90 (1/9 EtOAc:hexane); $^1$H NMR (300 MHz, CDCl$_3$) δ 7.57 (d, J=6.7 Hz, 4H), 7.41 (m, 6H), 5.88 (m, 1H), 5.00 (dd, J=17.0, 1.5 Hz, 1H), 4.92 (dd, J=10.2, 1.5 Hz, 1H), 3.44 (d, J=12.4 Hz, IH), 2.12 (m, 2H), 1.84 (m, 1H), 1.60 (t, J=12.5 Hz, 1H), 1.30 (m, 3H), 0.92 (d, J=6.7 Hz, 3H), 0.89 (d, J=6.7 Hz, 3H); $^{13}$C NMR (75 MHz, CDCl$_3$) δ 140.7, 135.3, 132.6, 129.9, 128.0, 113.3, 49.2, 38.8, 27.5, 25.9, 23.3, 20.7, 10.5; IR (neat) 3071 (w), 3051 (w), 2995 (w), 2957 (s), 2923 (m), 2866 (m), 2102 (s), 1642 (w), 1473 (w), 1432 (s), 1264 (m), 1188 (w), 1116 (s), 1004 (w), 915 (m), 743 (s), 701 (s) cm$^{-1}$; MS (FAB) m/e (rel. intensity) 350 (MH$^+$, 18), 323 (32), 322 (100), 321 (27), 320 (16), 315 (42), 306 (42), 252 (17), 251 (23), 237 (18), 236 (73), 223 (26), 208 (17); HRMS (FAB) calcd for C$_{21}$H$_{28}$N$_3$Si: 350.2053. found: 350.2040. Anal. Calcd for C$_{21}$H$_{27}$N$_3$Si: C, 72.16; H, 7.79; N, 12.02. Found: C, 71.99; H, 7.91; N, 11.60.

N-[1-(3-Buten-1-yl)diphenylsilyl]-3-methylbutyl]benzamide (28). To a solution of azide 35 (1.3 g, 3.72 mmol) in ethyl ether (50 mL) at 0° C. was added dropwise over 5 min lithium aluminum hydride (1 M in ether, 18.6 mmol), and the mixture was allowed to warm to rt over 10 min. After stirring for 30 min under argon, the reaction mixture was cooled to 0° C. and quenched successively with water (0.7 mL), 15% NaOH in water (0.7 mL), and water (2.1 mL). The mixture was filtered and the residue extracted twice with 20-mL portions of ethyl ether. The combined organic extracts were washed with saturated aqueous NaCl and dried over Na$_2$SO$_4$. Concentration in vacuo gave quantitatively crude amine 36 as a colorless oil. This amine was dissolved in CH$_2$Cl$_2$ (30 mL) and Et$_3$N (5.0 mL), and the solution was cooled to 0° C. To this solution was added dropwise over 5 min benzoyl chloride (0.52 g, 3.72 mmol), and the mixture was allowed to warm to rt. After stirring overnight under argon, the reaction mixture was quenched with 10% aqueous K$_2$CO$_3$ (20 mL). The organic layer was isolated and the aqueous layer extracted twice with 50-mL portions of CH$_2$Cl$_2$. The combined organic extracts were washed with saturated aqueous NaCl, dried over Na$_2$SO$_4$, and concentrated. Column chromatography over silica gel (1/9 EtOAc:hexane) gave pure amide 28 as a white crystalline solid (1.40 g, 88%): R$_f$=0.25 (1/9 EtOAc:hexane); mp 99–101° C.; $^1$H NMR (300 MHz, CDCl$_3$) δ 7.61 (m, 6H), 7.42 (m, 9H), 5.83 (m, 1H), 5.55 (d, J=10.3 Hz, 1H), 4.95 (dd, J=17.1, 1.6 Hz, 1H), 4.87 (dd, J=10.2, 1.6 Hz, 1H), 4.70 (dt, J=11.3, 3.1 Hz, 1H), 2.08 (m, 2H), 1.64 (m, 1H), 1.39 (m, 2H), 1.30 (br t, J=7.3 Hz, 2H), 1.03 (d, J=6.5 Hz, 3H), 0.74 (t, J=6.5 Hz, 3H); $^{13}$C NMR (75 MHz, CDCl$_3$)δ 167.1, 141.1, 135.8, 135.7, 135.2, 133.3, 132.5, 131.3, 130.1, 128.7, 128.4, 128.4, 126.8, 113.4, 40.9, 34.8, 27.2, 24.9, 23.6, 21.2, 10.6; IR (film) 3420 (w), 3302 (m, br), 3067 (m), 3051 (m), 2955 (s), 2923 (s), 2863 (m), 2845 (w), 1958 (w), 1894 (w), 1823 (w), 1640 (s), 1581 (m), 1519 (s), 1487 (s), 1429 (s), 1322 (s), 1189 (w), 1114 (s), 1001 (m), 912 (m), 744 (s), 706 (s) cm$^{-1}$; MS (FAB) m/e (rel. intensity) 428 (MH$^+$, 8), 427 (8), 426 (4), 384 (8), 373 (7), 372 (22), 370 (4), 352 (12), 351 (34), 350 (100); HRMS (FAB) calcd for C$_{28}$H$_{34}$NOSi: 428.2410. found: 428.2411. Anal. Calcd for C$_{28}$H$_{33}$NSiO: C, 78.64; H, 7.77; N, 3.28. Found: C, 78.28; H, 7.96, N, 3.22.

3-[[1-(benzoylamino)-1-(3-methylbutyl)]diphenylsilyl]propanoic acid (37). To a solution of olefin 28 (0.63 g, 1.46 mmol) in acetone (23 mL) was added 0.18 mL (2 mol %) of a 4 wt % solution of OsO$_4$ in water and Jones reagent (1.89 mL, 5.05 mmol). After stirring the mixture for 24 h at rt, 2-propanol (0.73 mL) was added followed by NaHSO$_3$ (0.22 g). The mixture was diluted with water (45 mL) and stirred until a dark-green, homogeneous solution was produced. This solution was diluted with water (90 mL) and extracted with six 50-mL portions of EtOAc. The combined organic extracts were dried over MgSO$_4$. Concentration in vacuo gave crude carboxylic acid 37 as a colorless solid (0.62 g, 96%): R$_f$=0.40 (EtOAc); $^1$H NMR (300 MHz, CDCl$_3$) δ 7.50 (m, 6H), 7.35 (m, 9H), 5.61 (d, J=10.2 Hz, 1H), 4.63 (dt, J=10.8, 3.5 Hz, 1H), 2.40 (m, 1H), 2.21 (m, 1H), 1.55 (m, 1H), 1.36 (m, 4H), 0.94 (d, J=6.4 Hz, 3H), 0.76 (d, J=6.5 Hz, 3H); IR (film) 3427 (w), 3320 (m, br), 3067 (m), 3049 (m), 2957 (s), 2925 (s), 2869 (m), 2630 (w, br), 1967 (w), 1903 (w), 1713 (s), 1630 (s), 1536 (s), 1430 (s), 1326 (m), 1267 (m), 1233 (m), 1114 (s), 878 (w), 707 (s) cm$^{-1}$; MS (FAB) m/e (rel. intensity) 446 (MH$^+$, 13), 374 (8), 373 (30), 372 (100), 369 (8), 368 (30), 352 (7), 319 (8), 259 (7), 199 (20); HRMS (FAB) calcd for C$_{27}$H$_{32}$NO$_3$Si: 446.2151. found: 446.2159.

N-[1-[Diphenyl[3-oxo-3-[(phenylmethyl)amino]propyl]silyl]-3-methyl-1-butyl]benzamide (29). To a solution of benzylamine (28 mg, 0.26 mmol) in DME (5 mL) at 0° C. was added 4-methylmorpholine (0.025 mL, 0.22 mmol), DEC (65 mg, 0.34 mmol), HOBT (30 mg, 0.22 mmol), and crude carboxylic acid 37 (100 mg, 0.22 mmol). After stirring for 30 min at 0° C. under argon, the mixture was allowed to warm to rt and stirred overnight. This mixture was concentrated in vacuo and partitioned between water (8 mL) and EtOAc (8 mL). The organic layer was isolated and the aqueous layer extracted twice with 8-mL portions of EtOAc. The combined organic extracts were washed successively with saturated aqueous NaHCO$_3$ (8 mL) and saturated aqueous NaCl, dried over Na$_2$SO$_4$, and concentrated. Flash chromatography over silica gel (2/3 EtOAc:hexane) and recrystallization from EtOAc gave pure diamide 29 as a colorless crystalline solid (96 mg, 80%): R$_f$=0.50 (2/3 EtOAc:hexane); mp 131–132° C.: $^1$H NMR (300 MHz, CDCl$_3$) δ 7.41 (m, 20H), 6.42 (t, J=5.2 Hz, 1H), 5.98 (d, J=10.1 Hz, 1H), 4.72 (m, 1H), 4.33 (d, J=5.8 Hz, 2H), 2.54 (m, 1H), 2.10 (m, 1H), 1.65 (m, 1H), 1.45 (m, 4H), 0.98 (d, J=6.5 Hz, 3H), 0.82 (d, J=6.5 Hz, 3H); $^{13}$C NMR (75 MHz, CDCl$_3$) δ 174.8, 167.3, 138.4, 135.6, 135.4, 134.6, 132.4, 131.4, 130.3, 130.2, 128.7, 128.4, 127.9, 127.4, 126.8, 43.4, 40.0, 34.9, 30.5, 25.0, 23.3, 20.9, 7.6; IR (film) 3413 (w), 3280 (s, br), 3065(m), 3027 (m), 2951 (s), 2925 (s), 2865 (m), 1958 (w), 1892 (w), 1818 (w), 1636 (s), 1541(s), 1491 (m), 1429 (m), 1324 (m), 1259 (m), 1178 (w), 1114 (m), 1029 (w), 1003 (w), 882 (w), 700 (s) cm$^{-1}$; MS (FAB) m/e (rel. intensity) 535 (MH$^+$, 30), 459 (7), 458 (31), 457 (87), 372 (16), 346 (7), 345 (29), 344 (100), 284 (8); HRMS (FAB) calcd for C$_{34}$H$_{38}$N$_2$O$_2$Si: 534.7724 (MH$^+$–1). found: 534.7719. Anal. Calcd for C$_{34}$H$_{38}$N$_2$SiO$_2$: C, 76.36; H, 7.16; N, 5.24. Found: C, 76.21; H, 7.19; N, 5.23.

Having established a synthetic route to a dipeptide mimic such as 29, replacement of the two phenyl groups on silicon with hydroxyl groups leads to a silanediol.

The synthesis of Silanediol 1 is shown in the scheme below.

The product 1 is obtained in solution and derivatized as trisiloxane 39 for purposes of characterization. A strong acid was used to hydrolyze the two phenyl groups and leave the rest of the molecule intact.

The synthesis of a silanediol is shown in the scheme below.

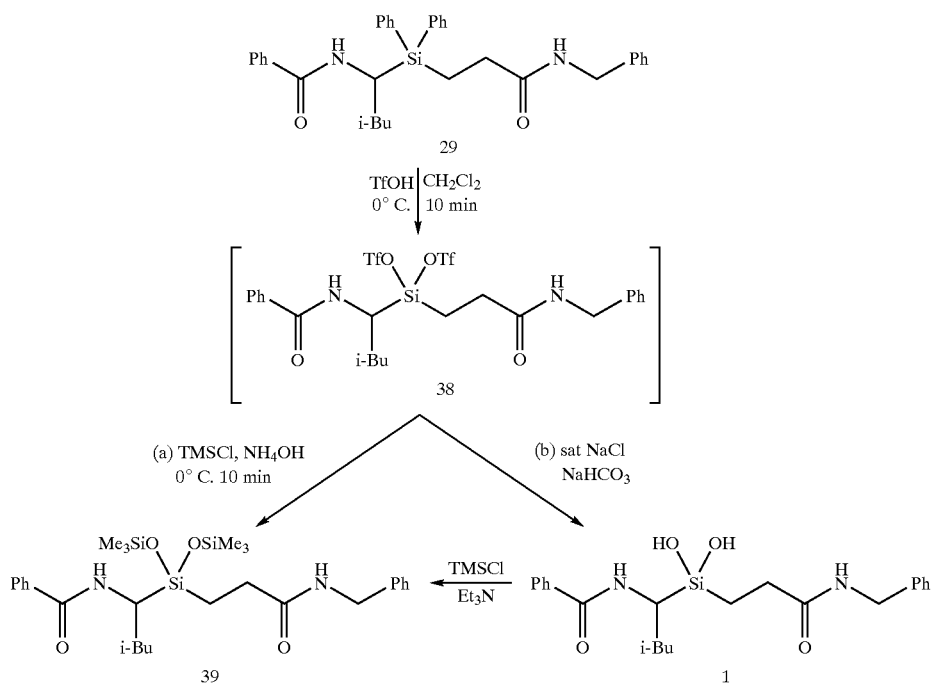

Scheme 4
Synthesis of Trisiloxane 39

N-[1-[[Bis-trimethylsilyloxy][3-oxo-3-(phenylmethylamino) propyl]silyl]-3-methyl-1-butyl] benzamide (39). To a solution of 29 (20 mg, 0.037 mmol) in CH$_2$Cl$_2$ (4.6 mL) at 0° C. was added triflic acid (0.44 mL, 5.0 mmol). After stirring for 10 min at 0° C. under nitrogen, the reaction mixture was diluted with CH$_2$Cl$_2$ (20 mL) and transferred via cannula to a second flask containing sat aqueous NaCl (20 mL) and NaHCO; (0.82 g, 10.0 mmol) at 0° C. This mixture was stirred for 15 min at 0° C. and the organic layer was isolated and dried with Na$_2$SO$_4$. The organic solution was cooled to 0° C. under nitrogen, and treated successively with TMSCl (3 mL) and Et$_3$N (2 mL). After stirring for 30 min at ° C., the mixture was quenched with water (10 mL). The organic layer was isolated and washed with sat aqueous NaCl, dried over Na$_2$SO$_4$, and concentrated. Flash chromatography over silica gel (1/2 EtOAc:hexane) gave trisiloxane 39 as a thick colorless oil (12 mg, 58% ): R$_f$=0.50 (1/3 EtOAc:hexane); $^1$H NMR (300 MHz, CDCl$_3$) δ 7.65 (d, J=7.1 Hz, 2H), 7.45–7.19 (m, 8H), 6.36–6.33 (m, 2H), 4.35 (d, J=5.7 Hz, 2H), 3.84–3.76 (m, 1H), 2.45–2.33 (m, 1H), 2.25–2.15 (m, 1H), 1.701–1.62 (m, 1H), 1.51–1.41 (m, 1H), 1.37–1.28 (m, 1H), 0.96–0.79 (m, 8H), 0.09 (s, 9H), 0.07 (s, 9H); $^{13}$C NMR (75 MHz, CDCl$_3$)

δ 174.4, 166.8, 138.4, 134.8, 131.1, 128.6, 128.5, 127.8, 127.3, 126.7, 43.6, 39.4, 37.7, 30.1, 25.2, 23.7, 21.5, 10.5, 2.0. 1.9; rR (neat) 3272 (m, br), 3066 (w), 3028 (w), 2956 (s), 2924 (w), 2865 (s), 1638 (s), 1539 (s), 1496 (w), 1330 (w), 1255 (s), 1177 (w), 1080 (s), 845 (s), 760 (m), 702 (m) cm$^{-1}$; MS (FAB) m/e (rel. intensity) 581 (MNa$^+$, 48), 471 (19), 470 (44), 469 (99), 396 (20), 370 (24), 369 (40), 368 (100), 296 (15), 208 (12), 207 (51); HRMS (FAB) calcd for $C_{28}H_{46}N_2O_4Si_3$.Na: 581.2662. found: 581.2662.

α-Silyl alcohol 46 was synthesized as shown in the scheme below.

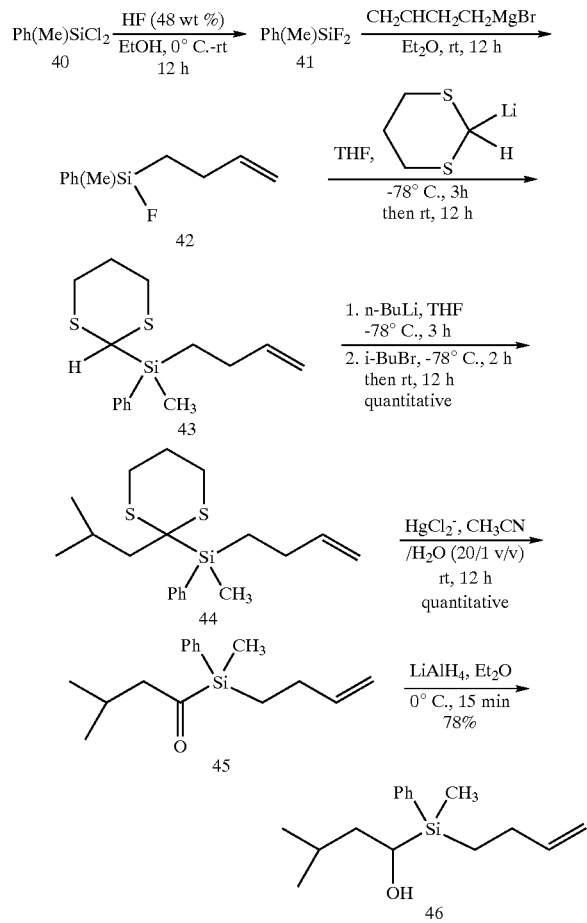

Scheme 5
Synthesis of α-Silyl Alcohol 46

Difluoromethylphenylsilane (41). To a solution of commercially available methylphenyldichlorosilane 40 (11.8 g, 61.5 mmol) in ethanol (200 mL) at 0° C. was added dropwise over 10 min hydrofluoric acid (48 wt % in water, 10 mL), and the mixture was allowed to warm to rt. After stirring overnight, the reaction mixture was poured into water (500 mL) and the resulting mixture extracted twice with 100-mL portions of hexane. The combined organic extracts were washed with saturated aqueous NaCl, dried over Na$_2$SO$_4$, and concentrated. The colorless oil of crude 41 was dissolved in toluene and concentrated under reduced pressure to remove any remaining moisture. This product was used in the next reaction without further purification: $^1$H NMR (300 MHz, CDCl$_3$) δ 7.68 (d, J=7.5 Hz, 2H), 7.6–7.55 (m, 1H), 7.48–7.44 (m, 2H), 0.62 (t due to fluorine, J=6.0 Hz, 3H).

(3-Buten-1-yl)fluoromethylphenylsilane (42). In a two-neck flask equipped with a condenser was placed magnesium (3 g, 123 mmol) and a crystal of iodine. The flask was warmed with heat gun until iodine had sublimed. A solution of 4-bromo-1-butene (9.13 g, 67.7 mmol) in ether (100 mL) was added dropwise over 30 min, and the mixture was refluxed for 2 h. This Grignard solution was cooled to rt and added over 30 min via cannula to a second flask containing 41 (9.72 g, 61.5 mmol) in toluene (100 mL) at rt. After stirring overnight at rt under argon, the reaction mixture was quenched with water (20 mL) and the organic layer isolated. The aqueous layer was extracted twice with 30-mL portions of EtOAc. The combined organic extracts were washed with saturated aqueous NaCl and dried over Na$_2$SO$_4$. Concentration in vacuo provided, quantitatively, crude 42 as a colorless oil. This product was used in the next reaction without further purification: R$_f$=0.75 (hexane): $^1$H NMR (300 MHz, CDCl$_3$) δ 7.60 (m, 2H), 7.40 (m, 3H), 5.88 (m, 1H), 5.04 (d, J=17.0 Hz, 1H), 4.95 (d, J=10.0 Hz, 1H), 2.19 (m, 2H), 1.05 (m, 2H), 0.52 (d due to fluorine, J=6.0 Hz, 3H).

(3-Buten-1-yl)(1,3-dithian-2-yl)methylphenylsilane (43). To a solution of 1,3-dithiane (11.1 g, 91.9 mmol) in THF (150 mL) at −78° C. was added dropwise over 10 min n-butyllithium (1.6 M in hexane, 76.6 mmol), and the solution was stirred for 2 h under argon. A solution of 42 (11.9 g, 61.3 mmol) in THF (120 mL) was added dropwise over 30 min, and the mixture was stirred for 3 h at −78° C. and overnight at rt. The reaction mixture was quenched with water (100 mL) and extracted thrice with 100-mL portions of EtOAc. The combined organic extracts were washed with saturated aqueous NaCl, dried over Na$_2$SO$_4$, and concentrated. Flash chromatography over silica gel (1/9 EtOAc:hexane) gave 43 contaminated with 1,3-dithiane. The latter was removed by sublimation (54° C., 8.0 mm Hg) to provide pure 43 as a yellow oil (9.0 g, 50% for three steps from dichlorosilane):R$_f$=0.55 (1/9 EtOAc:hexane), $^1$H NMR (300 MHz, CDCl$_3$) δ 7.63–7.61 (m, 2H), 7.42–7.38 (m, 3H), 5.97–5.84 (m, 1H), 5.06–4.90 (m,2H), 3.95 (s, 1H) 2.93–2.83 (m, 2H), 2.72–2.67 (m, 2H), 2.21–1.97 (m, 4H), 1.18–1.09 (m, 2H), 0.49 (s, 3H); $^{13}$C NMR (75 MHz, CDCl$_3$) δ 141.0, 134.5, 134.1, 129.9, 127.9, 113.2, 32.9, 31.1, 31.0, 27.2, 25.8, 10.8, −7.0; MS (FAB) m/e (rel. intentsity) 293 (MH+, 23), 239 (21), 175 (20), 159 (9), 149 (58), 121 (100), 119 (37), 115 (23), 105 (34), 97 (28), 92 (22); HRMS (FAB) calcd for $C_{15}H_{23}S_2Si$: 293.0854. found: 293.0861. Anal. Calcd for $C_{15}H_{22}S_2Si$: C, 61.16; H, 7.53. Found C, 61.31; H, 7.74.

(3-Buten-1-yl)methyl[2-(2-methyl-1-propyl)-1,3-dithian-2-yl]phenylsilane (44). To a solution of 43 (6.81 g, 23.1 mmol) in THF (150 mL) at −78° C. was added dropwise over 10 min n-butyllithium (1.6 M in hexanes, 23.1 mmol). After 3 h of stirring under argon, 1-bromo-2-methylpropane (3.52 mL, 32.3 mmol) was added dropwise over 5 min and the mixture stirred for 2 h at −78° C. and overnight at rt. The reaction mixture was quenched with water (10 mL) and extracted with three 100-mL portions of EtOAc. The combined organic extracts were washed with saturated aqueous NaCl and dried over Na$_2$SO$_4$. Concentration gave quantitatively 44 as a yellow oil. This product was used in the next reaction without further purification: R$_f$=0.75 (1/19 EtOAc:hexane); $^1$H NMR (300 MHz, CDCl$_3$) δ 7.69–7.66 (m, 2H), 7.40–7.33 (m, 3H), 5.93–5.82 (m, 1H), 4.99 (dd, J=17.0, 1.7 Hz, 1H), 4.88 (dd, J=10.1, 1.7 Hz, 1H), 3.0–2.91 (m, 2H), 2.50–2.40 (m, 2H), 2.13–1.90 (m, 6H), 1.78–1.70 (m, 1H), 1.31–1. 24 (m, 2H), 0.94 (d, J=6.6 Hz, 3H), 0.84 (d, J=6.6 Hz, 3H), 0.55 (s, 3H); $^{13}$C NMR (75 MHz, CDCl$_3$) δ 141.2, 135.1, 134.5, 129.5, 127.5, 112.9, 45.6, 39.5, 27.9, 27.0, 24.7, 24.6, 24.2, 24.1, 11.5, −6.1; IR (neat) 3067 (m), 3047 (m), 2995 (m), 2972 (m), 2896 (s), 2845 (m), 1957 (w), 1886 (w), 1823 (w), 1641 (m), 1430 (s), 1276 (m), 1254 (s), 1168 (m), 1114 (s), 1086 (m), 1002 (m), 910 (s), 798 (s), 739 (s), 700 (s) cm$^{-1}$; MS (CI/CH$_4$) m/e (rel. intensity) 351 (MH$^+$, 19), 350 (21), 335 (24), 297 (15), 296 (25), 295 (100), 275 (12), 274 (16), 273 (71), 205 (15), 175 (36), 149 (74); HRMS (FAB) calcd for C$_{19}$H$_{30}$S$_2$Si: 350.1558 (MH$^+$−1 ). found: 350.1561.

1-[(3-Buten-1-yl)methylphenylsilyl]-3-methyl-1-butanone (45). To a solution of 44 (6.19 g, 17.7 mmol) in CH$_3$CN (200 ml) was added water (10 mL) and HgCl$_2$ (24 g, 88 mmol). After stirring overnight at rt, the mixture was concentrated and partitioned between water (100 mL) and hexane (200 mL). The organic layer was isolated and the aqueous layer extracted twice with 50-mL portions of hexane. The combined organic extracts were washed with saturated aqueous NaCl and dried over Na$_2$SO$_4$. Concentration to dryness in vacuo at rt gave quantitatively crude ketone 45 as a yellow oil. This ketone was used in the next reaction without further purification: R$_f$=0.75 (1/19 EtOAc:hexane); $^1$H NMR (300 MHz, CDCl$_3$) δ 7.54–7.51 (m, 2H), 7.41–7.35 (m, 3H), 5.91–5.78 (m, 1H), 4.99 (dd, J=17.0, 1.7 Hz, 1H), 4.90 (dd, J=10.0, 1.7 Hz, 1H), 2.44 (d, J=6.7 Hz, 2H), 2.16–2.06 (m, 3H), 1.16–1.07 (m, 2H), 0.78 (pd, J=6.7 Hz, 6H), 0.51 (s, 3H).

1-[(3-Buten-1-yl)methylphenylsilyl]-3-methyl-1-butanol (46). To a solution of 45 (4.60 g, 17.7 mmol) in ethyl ether (150 mL) at 0° C. was added dropwise over 5 min lithium aluminum hydride (1 M in ethyl ether, 88.3 mmol). After stirring for 15 min at 0° C. under argon, the reaction mixture was diluted with ethyl ether (200 mL) and quenched with saturated Na$_2$SO$_4$ solution until evolution of hydrogen had ceased. The mixture was dried with solid Na$_2$SO$_4$ and filtered. The residue was extracted with ether (50 mL) and the organic extracts combined. Concentration provided a yellow oil of 46 as a mixture of diastereomers (3.6 g, 78%). This product was used in the next reaction without further purification: R$_f$=0.50 (1/9 EtOAc:hexane); $^1$H NMR (300 MHz, CDCl$_3$) δ 7.58–7.53 (m, 2H), 7.39–7.34 (m, 3H), 5.95–5.82 (m, 1H), 5.03–4.89 (m, 2H), 3.70 (dd, J=12.0, 2.3 Hz, 1H), 2.15–2.07 (m, 2H), 1.86–1.76 (m, IH), 1.59–1.49 (m, 2H), 1.23–1.12 (m, 1H), 1.03–0.84 (m, 7H), 0.33 and 0.34 (two singlets due to diastereomers, 3H); $^{13}$C NMR (75 MHz, CDCl$_3$) δ 141.5, 135.8, 135.6, 134.7, 134.6, 129.6, 129.5, 128.2, 128.1, 113.2, 62.5, 62.1, 42.3, 42.2, 27.5, 24.2, 24.1, 23.6, 20.7, 20.8, 10.7, 10.5, −7.9, −8.0; IR (neat) 3571 (w), 3434 (m, br), 3069 (m), 2954 (s), 2913 (s), 2872 (m), 1638 (m), 1466 (m), 1427 (m), 1366 (w), 1251 (m), 1111 (s), 993 (m), 902 (m), 790 (s), 736 (s), 700 cm$^{-1}$; MS (CI/CH$_4$) m/e (rel. intensity) 263 (M$^+$+1, 2), 247 (13), 235 (10), 233 (12), 231 (13), 207 (13), 187 (11), 177 (20), 176 (15), 175 (69), (69), 151 (23), 137 (100), 131 (12), 115 (41). Anal. Calcd for C$_{16}$H$_{26}$OSi: C, 73.22; H, 9.98. Found: C, 72.85; H, 10.24.

Another dipeptide mimic 51 was synthesized according to the scheme below.

Scheme 6
Synthesis of Dipeptide Mimic 51

1. MsCl, CH$_2$Cl$_2$
Et$_3$N, 0° C.-rt, 12 h
46
2. NaN$_3$, DMF
rt, 12 h 84%

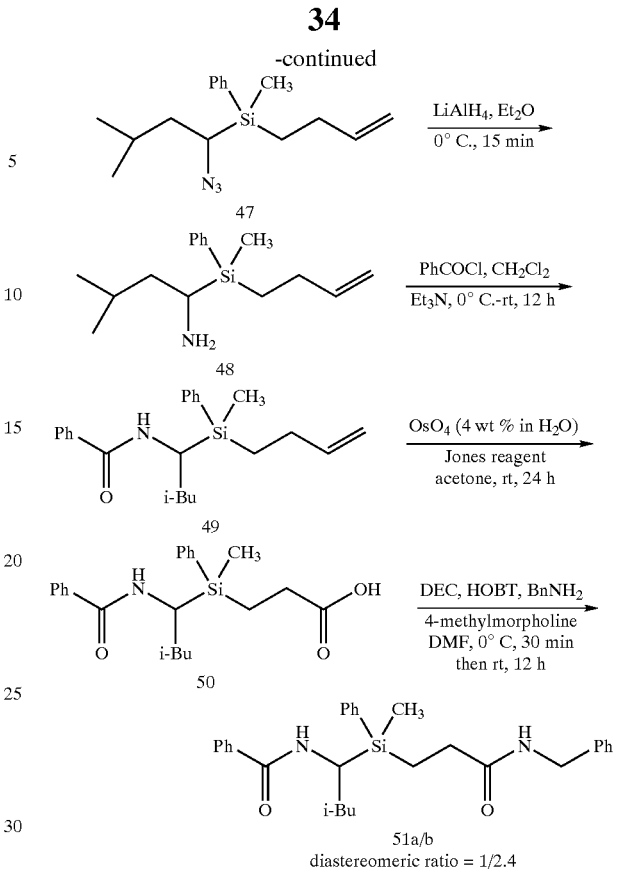

(1-Azido-3-methyl-1-butyl)(3-buten-1-yl)methylphenylsilane (47). To a solution of 46 (3.4 g, 13 mmol) in CH$_2$Cl$_2$ (150 mL) and Et$_3$N (9 mL, 65 mmol) at 0° C. was added dropwise over 5 min methanesulfonyl chloride (7.4 g, 65 mmol), and the mixture was allowed to warm to rt over 1 h. After siring overnight under argon, the mixture was cooled to 0° C. and quenched with water (50 mL). The organic layer was isolated and the aqueous layer extracted twice with 50-mL portions of CH$_2$Cl$_2$. The combined organic extracts were concentrated in vacuo at rt. The crude mesylate was dissolved in DMF (150 mL), and to this solution was added sodium azide (4.2 g, 64.8 mmol). After stirring overnight at rt, the mixture was partitioned between water (200 mL) and EtOAc (200 ml). The organic layer was isolated and the aqueous layer extracted twice with 50-mL portions of EtOAc. The combined organic extracts were washed with saturated aqueous NaCl, dried over Na$_2$SO$_4$, and concentrated. Flash chromatography over silica gel (1/19 EtOAc:hexane) gave a colorless oil of pure 47 as a mixture of diastereomers (3.11 g, 84%): R$_f$=0.80 (1/9 EtOAc:hexane); $^1$H NMR (300 MHz, CDCl$_3$) δ 7.53–7.47 (m, 2H), 7.38–7.32 (m, 3H), 5.91–5.78 (m, 1H), 5.0–4.86 (m, 2H), 3.03 and 2.99 (two triplets due to diastereomers, J=2.7 Hz, 1H), 2.08 (q, J=7.8 Hz, 2H), 1.82–1.70 (m, 1H), 1.58–1.47 (m, 1H), 1.19–1.10 (m 1H), 1.06–0.94 (m, 2H), 0.89–0.83 (m, 6H), 0.38 and 0.36 (two singlets due to diastereomers, 3H); 13C NMR (75 MHz, CDCl$_3$) δ 140.8, 134.2, 134.1, 129.6, 128.0, 113.3, 50.4, 50.3, 38.6, 38.5, 27.5, 25.8, 23.3, 20.7, 11.4, 11.0, −6.8, −7.3; IR (neat) 3067 (w), 2956 (s), 2914 (m), 2865 (m), 2099 (s), 1640 (m), 1469 (w), 1427 (m), 1259 (s), 1113 (m), 999 (w), 909 (m), 795 (m), 738 (m), 699 (m) cm$^{-1}$; MS (FAB) m/e (rel. intensity) 288 (MH$^+$, 19), 262 (10), 261 (32), 260 (100), 259 (29), 258 (39), 253 (14), 245 (20), 244 (64), 233 (15), 217 (11), 216

(16), 207 (19), 204 (54); HRMS (FAB) calcd for $C_{16}H_{26}N_3Si$: 288.1896. found: 288.1895.

N-[1-[(3-Buten-1-yl)methylphenylsilyl]-3-methyl-1-butyl]benzamide (49). To a solution of azide 47 (2.75 g, 9.57 mmol) in ethyl ether (100 mL) at 0° C. was added dropwise over 5 min lithium aluminum hydride (1 M in ether, 47.8 mmol), and the mixture was allowed to warm to rt over 10 min. After stirring for 30 min under argon, the mixture was cooled to 0° C. and diluted with ether (100 mL). This mixture was quenched with saturated aqueous $Na_2SO_4$ solution until evolution of hydrogen had ceased. The mixture was dried with solid $Na_2SO_4$ and filtered. The residue was extracted with ether (50 mL) and the organic extracts combined. Concentration gave crude amine 48 as a colorless oil. This amine was dissolved in $CH_2Cl_2$ (60 mL) and $Et_3N$ (5 mL), and the solution was cooled to 0° C. To this solution was added dropwise over 5 min benzoyl chloride (1.34 g, 9.57 mmol), and the mixture was allowed to warm to rt. After stirring overnight under argon, the reaction mixture was quenched with saturated aqueous $NaHCO_3$ (20 mL). The organic layer was isolated and the aqueous layer extracted twice with 50-mL portions of $CH_2Cl_2$. The combined organic extracts were washed with saturated aqueous NaCl, dried over $Na_2SO_4$, and concentrated. Flash chromatography over silica gel (1/9 EtOAc:hexane) gave a sticky colorless solid of 49 as a mixture of diastereomers (2.6 g, 74%): $R_f$=0.20 (1/9 EtOAc:hexane); $^1$H NMR (300 MHz, $CDCl_3$) δ 7.69–7.60 (m, 2H), 7.56–7.54 (m, 2H), 7.48–7.37 (m, 6H), 5.95–5.80 (m, 1H), 5.57 (d, J=9.9 Hz, 1H), 5.0 (d, J=17.0 Hz, 1H), 4.90 (d, J=8.6 Hz, IH), 4.24–4.13 (m, 1H), 2.17–2.07 (m, 2H), 1.68–1.55 (m, 1H), 1.44–1.24 (m, 2H), 1.07–0.99 (m, 2H), 0.93 (d, J=6.4 Hz 3H), 0.85 and 0.84 (two doublets due to diastereomers, J=6.6 Hz, 3H), 0.40 and 0.39 (two singlets due to diastereomers, 3H); $^{13}$C NMR (75 Mhz, $CDCl_3$) δ 166.7, 140.9, 135.0, 134.7, 134.5, 134.34, 134.31, 131.1, 131.0, 130.5, 129.64, 129.61, 128.8, 128.54, 128.50, 128.0, 126.6, 113.3, 113.2, 40.5. 40.4, 37.2, 36.9, 27.5, 25.1, 23.6, 21.2, 11.3, 10.7, -6.7, -7.4; IR (neat) 3279 (m, br), 3064 (m), 2954 (s), 2919 (m), 2867 (m), 1787 (w), 1727 (w), 1628 (s), 1577 (m), 1536 (s), 1487 (mn), 1427 (m), 1323 (m), 1252 (m), 110 (m), 994 (m), 902 (m), 791 (m), 699 (s) cm$^{-1}$; MS (FAB) m/e (rel. intensity) 366 (MH$^+$, 11), 365 (9), 364 (5), 350 (6), 322 (11), 311 (11), 310 (34), 290 (10), 289 (26), 288 (100), 253 (8); HRMS (FAB) calcd for $C_{23}H_{31}NOSi$: 365.2175 (MH$^+$-1). found: 365.2172. Anal. Calcd for $C_{23}H_{31}NOSi$: C, 75.56; H, 8.55; N; 3.83. Found: C, 75.18; H, 8.41; N, 3.72.

3-[[1-(Benzoylamino)-3-methylbutyl]methylphenylsilyl] propanoic acid (50). To a solution of 49 (0.7 g, 1.91 mmol) in acetone (22 mL) was added 0.23 mL (2 mol %) of a 4 wt % solution of $OsO_4$ in water and Jones reagent (2.43 mL, 6.49 mmol). After stirring the mixture for 24 h at rt, 2-propanol (0.5 mL) was added followed by $NaHSO_3$ (0.2 g). The mixture was diluted with water (50 mL) and stirred until a dark-green, homogeneous solution was produced. This solution was diluted further with water (90 mL) and extracted with six 50-mL portions of EtOAc. The combined organic extracts were washed with saturated aqueous NaCl and dried over $Na_2SO_4$. Concentration cave a colorless solid of crude 50 as a mixture of diastereomers. This product was used in the next reaction without further purification: $R_f$=0.20 (1/9 EtOAc:hexane); $^1$H NMR (300 MHz, $CDCl_3$) δ 7.67–7.62 (m, 2H), 7.54–7.52 (m, 2H), 7.48–7.37 (m, 6H), 5.79 and 5.73 (two doublets due to diastereomers, J=10.0 Hz, 1H), 4.25–4.13 (m, 1H), 2.44–2.34 (m, 2H), 1.64–1.57 (m, 1H), 1.49–1.38 (m, 1H), 1.34–1.21 (m, 3H), 1.03, 0.98, 0.90 and 0.84 (four doublets due to diastereomers, J=6.6 Hz, 6H), 0.40 (s, 3H); MS (FAB) m/e (rel. intensity) 384 (MH$^+$, 62), 315 (7), 312 (8), 311 (27), 310 (100), 307 (19), 306 (88), 255 (10), 253 (22); HRMS (FAB) calcd for $C_{22}H_{30}NO_3Si$: 384.1995. found: 384.1995.

N-[3-Methyl-1-[methylphenyl[3-oxo-3-(phenylmethylamino)-1-propyl)silyl]-1-butyl]benzamide (51). To a solution of benzylamine (0.25 g, 2.29 mmol) in DMF (25 mL) at 0° C. was added 4-methylmorpholine (0.21 mL, 1.91 mmol), DEC (0.55 g, 2.87 mmol), HOBT (0.26 g, 1.91 mmol), and crude carboxylic acid 50 (1.91 mmol of starting olefin). After stirring for 30 min at 0° C. under argon, the mixture was allowed to warm to rt and stirred overnight. This mixture was partitioned between water (30 mL) and EtOAc (30 mL). The organic layer was isolated and the aqueous layer extracted twice with 30-mL portions of EtOAc. The combined organic extracts were washed successively with saturated aqueous $NaHCO_3$ (20 mL) and saturated aqueous NaCl, dried over $Na_2SO_4$, and concentrated. Flash chromatography over silica gel (1/1/3 EtOAc:hexane: $CH_2Cl_2$) gave two diastereomers: 51a as a colorless crystalline solid (0.18 g, less polar) and 51b as a white powdery solid (0.44 g). Overall yield, 69% from the olefin.

51a: $R_f$=0.50 (1/1 EtOAc:hexane); mp 42–44° C.; $^1$H NMR (300 MHz, $CDCl_3$) δ 7.60 (d, J=7.3 Hz, 2H), 7.53–7.25 (m, 13H), 6.56 (t, J=5.3 Hz, 1H), 6.13 (d, J=10.1 Hz, 1H), 4.40 (d, J=5.7 Hz, 2H), 4.41 (m, 1H), 2.63–2.52 (m, 1H), 2.37–2.27 (m, 1H), 1.65–1.55 (m, 1H), 1.45 (dt, J=14.1, 3.6 Hz, 1H), 1.35–1.21 (m, 3H), 0.88 (d, J=6.4 Hz, 3H), 0.85 (d, J=6.6 Hz, 3H), 0.37 (s, 3H); $^{13}$C NMR (75 MHz, $CDCl_3$) δ 174.9, 167.1, 138.5, 134.8, 134.6, 134.4, 131.4, 129.9, 128.8, 128.7, 128.3, 128.0, 127.4, 126.8, 43.5, 39.4, 36.6, 30.6, 25.0, 23.3, 20.9, 7.6, -7.1; IR (film) 3284 (br, s), 3063 (m), 2950 (m), 2926 (m), 2868 (w), 1636 (s), 1539 (s), 1491 (w), 1427 (w), 1325 (m), 1252 (m), 1109 (m), 793 (m), 734 (w), 698 (s) cm$^{-1}$; MS (FAB) m/e (rel. intensity) 473 (MH$^+$, 58), 396 (22), 395 (72), 310 (18), 283 (24), 282 (100), 157 (72), 137 (30), 105 (23), 91 (68); HRMS (FAB) calcd for $C_{29}H_{37}N_2O_2Si$: 473.2624. found: 473.2625. Anal. Calcd for $C_{29}H_{36}N_2O_2Si$—$H_2O$: C, 70.98; H, 7.81; N, 5.71. Found: C, 71.20; H, 7.49; N, 5.76.

51b: $R_f$=0.45 (1/1 EtOAc:hexane); mp 190–191° C.; $^1$H NMR (300 MHz, $CDCl_3$) δ 7.66 (d, J=7.4 Hz, 2H), 7.54–7.21 (m, 13H), 6.10–6.06 (m, 2H), 4.37 (d, J=5.6 Hz, 2H), 4.32–4.24 (m, 1H), 2.45–2.35 (m, 1H), 2.24–2.13 (m, 1H), 1.68–1.59 (m, 1H), 1.48 (dt, J=14.4, 3.5 Hz, 1H), 1.33–1.15 (m, 3H), 0.91 (d, J=6.5 Hz, 3H), 0.85 (d, J=6.5 Hz, 3H), 0.37 (s, 3H); $^{13}$C NMR (75 MHz, $CDCl_3$) δ 174.5, 167.4, 138.6, 135.0, 134.6, 134.5, 131.5, 130.0, 128.9, 128.8, 128.4, 128.1, 127.6, 126.9, 43.6, 40.0, 36.6, 30.7, 25.1, 23.5, 21.0, 8.7, -7.4; IR (nujol) 3261 (m), 2949 (s), 2922 (s), 2854 (s), 1652 (m), 1628 (m), 1559 (m), 1459 (m), 1376 (m), 733 (w), 699 (m) cm$^{-1}$; MS (FAB) m/e (rel. intensity) 473 (MH$^+$, 32), 395 (47), 282 (58), 232 (22), 171 (27), 157 (100),137 (48), 136 (24), 93 (42), 91 (46); HRMS (FAB) calcd for $C_{29}H_{37}N_2O_2Si$: 473.2624. found: 473.2621; Anal. Calcd for $C_{29}H_{36}N_2O_2Si \cdot 0.2H_2O$: C, 73.13; H, 7.70; N, 5.88. Found: C, 73.09; H, 7.49; N, 5.96.

A methylsilanol was made according to the scheme below.

Scheme 7
Synthesis of Methysilanol 2

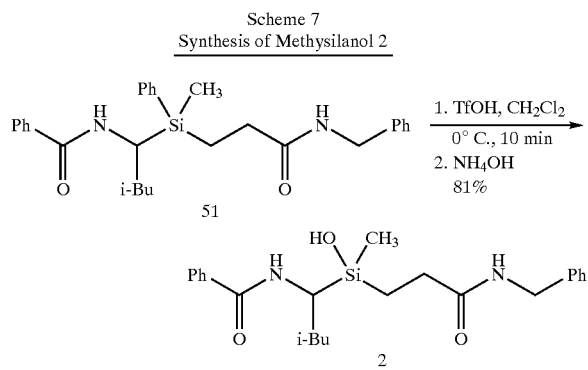

N-[1-Hydroxy(methyl)[3-oxo-3-(phenylmethylamino)-1-propyl]silyl]-3-methylbutyl]benzamide (2). To a solution of 51b (88 mg, 0.18 mmol), one of the diastereomers of 51, in $CH_2Cl_2$, (30 mL) at 0° C. was added triflic acid (3 mL, 34 mmol). After stirring the mixture for 10 min under argon, saturated aqueous $NH_4OH$ (30 mL) was added. The organic layer was isolated and the aqueous layer extracted twice with 5-mL portions of $CH_2Cl_2$. The combined organic extracts were washed with saturated aqueous NaCl, dried over $Na_2SO_4$ and concentrated at rt. The crude product was run through a short path of silica gel, about one inch long, and eluted with EtOAc. Concentration provided a white solid of methylsilanol 2 as a mixture of diastereomers (61 mg, 81%). Attempts to separate the diastereomers were unsuccessful. But the diastereomers were separated as the disiloxanes below. The diastereomeric ratio was determined by $^1H$ NMR to be 1:1.6: $R_f$=0.10 (1/1 EtOAc:hexane); mp 35–36° C.; $^1H$ NMR (300 MHz, $CDCl_3$) δ 7.72–7.67 (m, 2H), 7.45–7.13 (m, 8H), 6.73 and 6.60 (two doublets due to diastereomers, J=8.3 Hz, 1NH), 6.35–6.24 (m, INH), 4.39–4.24 (m, 3H), 3.67–3.55 (m, 1H), 2.42–2.30 (m, 2H), 1.73–1.60 (m, 2H), 1.38–1.17 (m, 2H), 0.89 (d, J=6.4 Hz 6H), 0.14 and 0.05 (two singlets due to diastereomers, 3H); $^{13}C$ NMR (75 MHz, $CDCl_3$) δ 174.7, 167.8, 167.6, 164.2, 138.1, 138.0, 134.7, 134.6, 131.3, 131.2, 128.7, 128.6, 128.5, 127.8, 127.72, 127.69, 127.50, 127.47, 127.4, 126.9, 43.7, 43.6, 40.0, 39.7, 39.0, 38.9, 30.3, 30.1, 25.4, 25.3, 23.6, 21.3, 10.9, 10.0, 1.0, –3.1, –3.3; IR (film) 3288 (br, m), 3068 (w), 3032 (w), 2954 (m), 2926 (m), 2869 (w), 1636 (s), 1543 (s), 1496 (w), 1451 (w), 1325 (w), 1262 (m), 1084 (w), 1033 (w), 888 (m), 879 (m), 804 (m), 704 (s) cm-1; MS (FAB) m/e (rel. intensity) 435 (MNa+, 100), 413 (1), 306 (6), 290 (5), 242 (4), 107 (15), 101 (92); HRMS (FAB) calcd for $C_{23}H_{32}N_2O_3Si\cdot Na$: 435.2080. found: 435.2071.

A disiloxane 52 was made according to the following scheme.

Scheme 8
Synthesis of Disiloxane 52

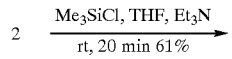

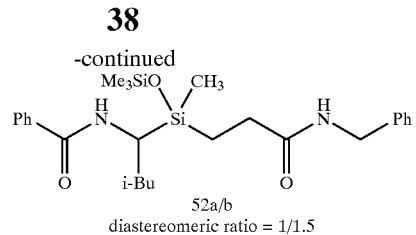

52a/b
diastereomeric ratio = 1/1.5

[3-methyl-1-[methyl[3-oxo-3[(phenylmethyl)amino]propyl][(trimethyl silyl)oxy]silyl]butyl]benzamide (52). To a solution of 2 (75 mg, 0.18 mmol) in THF (10 mL) at rt was added $Et_3N$ (1 mL) and TMSCI (1 mL), and the mixture was stirred for 20 min. This mixture was concentrated in vacuo and then partitioned between water (5 mL) and $CH_2Cl_2$ (5 mL). The organic layer was isolated and the aqueous layer extracted twice with 5-mL portions of $CH_2Cl_2$. The combined organic extracts were washed with saturated aqueous NaCl, dried over $Na_2SO_4$, and concentrated. Purification by thin layer chromatography (1/3 EtOAc:hexane) gave two diastereomers: 52a as a clear sticky solid (21 mg, less polar) and 52b as a clear sticky solid (33 mg). Overall yield, 60% for two steps from 51b.

52a: $R_f$=0.25 (1/3 EtOAc:hexane); 1H NMR (300 MHz, $CDCl_3$) δ 7.72 (d, J=17.2 Hz, 2H), 7.49–7.22 (m, 8H), 6.58 (d, J=9.7 Hz, 1H), 6.37 (t, J=4.8 Hz, 1H), 4.38 (d, J=5.6 Hz, 2H), 3.86 (m, 1H), 2.45–2.34 (m, 1H), 2.31–2.20 (m, 1H), 1.75–1.66 (m, 1H), 1.55 (dt, J=14.1, 3.8 Hz, 1H), 1.38–1.29 (m, 1H), 1.26–0.86 (m, 8H), 0.14 (s, 3H), 0.10 (s, 9H); $^{13}C$ NMR (75 MHz, $CDCl_3$) δ 174.4, 166.8, 138.2, 134.7, 131.1, 128.6, 128.5, 127.7, 127.3, 126.7, 43.6, 39.3, 38.3, 30.1, 25.2, 23.6, 21.3, 11.0, 1.9, –2.9; IR (neat) 3277 (br, s), 3061 (w), 3032 (w), 2955 (s), 2923 (m), 2865 (w), 1635 (s), 1544 (s), 1492 (m), 1460 (w), 1329 (m) 1254 (s), 1177 (w), 1066 (s), 848 (s), 757 (w), 703 (s) cm$^{-1}$; MS (FAB) m/e (rel. intensity) 507 (MNa+, 100), 469 (4), 397 (5), 396 (18), 395 (55) 322 (8), 296 (6), 295 (13), 294 (50), 222 (4); HRMS (FAB) calcd for $C_{26}H_{40}N_2O_3Si_2$—Na: 507.2475. found: 507.2473.

52b: $R_f$=0.20 (1/3 EtOAc:hexane); $^1H$ NMR (300 MHz, $CDCl_3$) δ 7.62 (d, J=7.1 Hz, 2H), 7.44–7.18 (m, 8H), 6.38 (t, J=5.5 Hz, 1H), 6.27 (d, J=9.2 Hz, 1H), 4.34 (d, J=5.4 Hz, 2H), 3.88–3.80 (m, 1H), 2.47–2.37 (m, 1H), 2.26–2.15 (m, 1H), 1.73–1.6 (m, IH, 1.49 (dt, J=14.2, 4.0 Hz, 1H), 1.35–1.26 (m, 1H), 1.02–0.76 (m, 8H), 0.09 (s, 3H), 0.04 (s, 9H); $^{13}C$ NMR (75 MHz, $CDCl_3$) δ 174.5, 167.0, 138.3, 134.7, 131.1, 128.6, 128.5, 127.8, 127.3, 126.6, 43.5, 39.4, 38.2, 30.2, 25.3, 23.6, 21.3, 11.2, 1.9, –3.1; IR (film) 3278 (br, s), 3063 (w), 3028 (w), 2954 (s), 2920 (m), 2868 (w), 1633 (s), 1547 (s), 1495 (m), 1460 (w), 1330 (m) 1259 (s), 1180 (w), 1074 (s), 846 (s), 704 (s) cm$^{-1}$; MS (FAB) m/e (rel. intensity) 507 (MNa+, 31), 469 (7), 408 (8), 397 (11), 396 (33), 395 (100), 329 (9), 296 (10), 295 (15), 294 (35), 257 (15), 237 (17); HRMS (FAB) calcd for $C_{26}H_{40}N_2O_3Si_2Na$: 507.2475. found: 507.2478.

Synthesis of HIV-1 protease inhibitor Dibenzyl-2-(S)-6-(S)-dibenzyl-4,4-dihydroxy-4-silaheptanediamide 9a is shown in the scheme below.

Scheme 9
Synthesis of Dibenzyl-2-(S)-6-(S)-dibenzyl-4,4-dihydroxy-4-silaheptanediamide (9a)

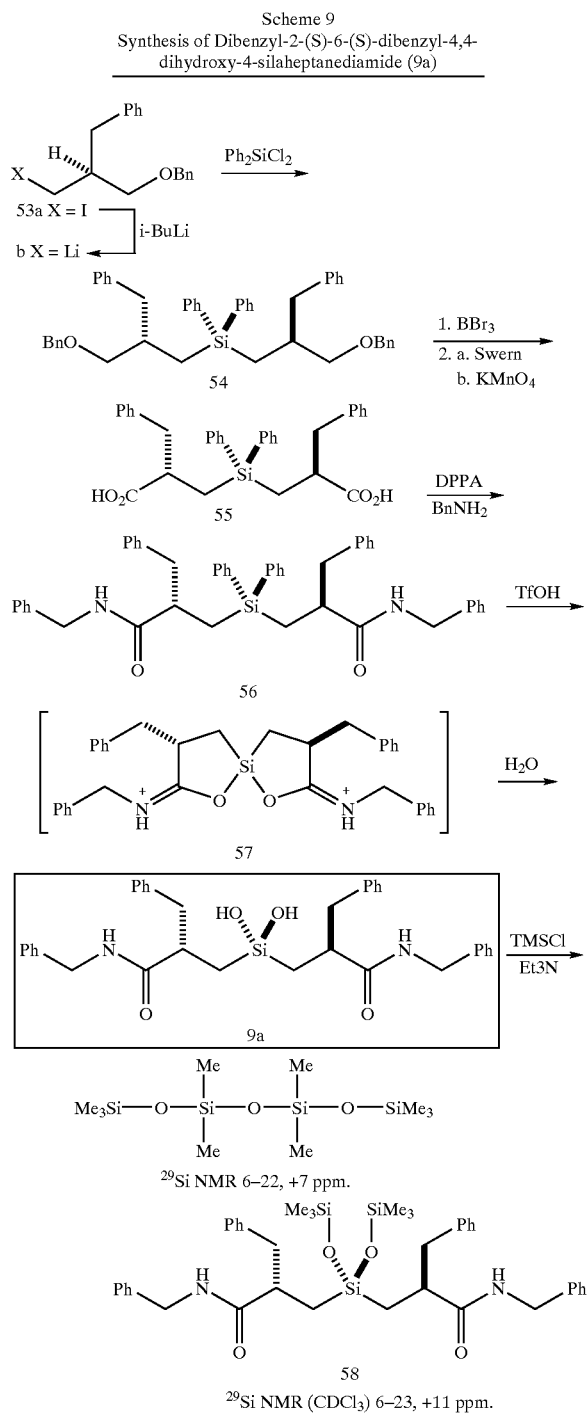

$^{29}$Si NMR 6–22, +7 ppm.

$^{29}$Si NMR (CDCl$_3$) 6–23, +11 ppm.

2-(S)-6-(S)-Dibenzyl-1,7-dibenzyloxy-4,4-diphenyl-4-sila-heptane (54). To a solution of 1-iodo-2-(S)benzyl-3-benzyloxypropane 53a (455 mg, 1.24 mmol) in 12 mL ether at −78° C. was added t-BuLi (1.5 M in pentane, 1.73 ) mL, 2.6 mmol). Stirring was continued at −78° C. for an additional 5 min following the addition, the cooling bath was then removed, and the mixture was allowed to warm and stand at room temperature for 40 min. The mixture was then recooled to 0° C. and dichlorodiphenylsilane (0.43 mmol, 0.9 mL) was added. After stirring for 3 h at 0° C., the mixture was warmed to room temperature overnight. After addition of saturated NH$_4$Cl (12 mL), the organic layer was dried over MgSO$_4$, filtered, and concentrated. Flash chromatography (40/1 hexane:ethyl acetate) afforded 54 as a pale yellow oil (280 mg, 98%); R$_f$=0.2 (40/1 hexane:ethyl acetate); IR (neat) 3063, 3025, 2854, 2359, 2341, 1494, 1453, 1427, 1307, 1108, 1036, 736, 698 cm$^{-1}$; $^1$H NMR (250 MHz, CDCl$_3$) δ 7.53–6.97 (m, 30H), 4.25 (s, 4H), 3.1 (d, 4H, J=4.9 Hz), 2.70 (dd, 2H, J=13.3, 7.9 Hz), 2.51 (dd, 2H, J=13.3, 6.8 Hz), 2.04 (m, 2H), 1.36 (dd, 2H, J=15.1, 7.7 Hz), 1.20 (dd, 2H, J=15.1, 5.9 Hz); $^{13}$C NMR (CDCl$_3$, 63 MHz) δ 140.7, 138.7, 136.3, 135.0, 129.3, 129.1, 128.2, 128.0, 127.8, 127.5, 127.3, 125.6, 73.5, 72.6, 40.8, 36.8, 15.3. Anal. Calcd for C$_{46}$H$_{48}$O$_2$Si: C, 83.59; H 7.32. Found: C, 83.62; H, 7.38. HRMS (FAB) calcd for C$_{46}$H$_{49}$O$_2$Si: 661.3502. found: 661.3500.

2-(S)-6-(S)-Dibenzyl-4,4-diphenyl-4-sila-1,7-heptanediol. To a −78° C. solution of 54 (290 mg, 0.44 mmol) in 20 mL CH$_2$Cl$_2$ was added BBr$_3$ (1M in CH$_2$Cl$_2$, 1.3 mL, 3 eq). After stirring for 2.5 h, the mixture was quenched by addition of methanol (10 mL) and after 30 min the mixture was warmed to room temperature. The solvent was removed on a rotary evaporator and the residue was partitioned between CH$_2$Cl$_2$ (20 mL) and water (20 mL). The organic layer was dried over MgSO$_4$, filtered and concentrated. Flash chromatography (7/3 hexane:ethyl acetate) afforded the title compound as a foam (196 mg, 93%). R$_f$=0.23 (7/3 hexane:ethyl acetate); $^1$H (300 MHz, CDCl$_3$) δ 7.47–6.94 (m, 20H), 3.43 (dd, 2H, J=10.8, 4.5 Hz), 3.29 (dd, 2H, J=10.8, 4.8Hz), 2.48 (m, 4H), 1.86–1.82 (m, 4H), 1.39 (dd, 2H, J=15, 7.2 Hz), 1.17 (dd, 2H, J=15, 5.7 Hz). HRMS (CI) calcd for C$_{32}$H$_{40}$NO$_2$Si (MNH$_4^-$) 498.2828. found: 498.2812.

2-(S)-6-(S)-Dibenzyl-4,4-diphenyl-4-sila-heptanedioic acid (55) To a −78° C. solution of distilled oxalyl chloride (0.9 mL, 10.3 mmol) in 20 mL CH$_2$Cl$_2$ was slowly added DMSO (1.46 mL, 20.6 mmol) and the mixture was stirred for 10 min. 2-(S)-6-(S)-Dibenzyl-4,4-diphenyl-4-sila-1,7-heptanediol (493 mg, 1.03 mmol) was added dropwise using two 10 mL portions of CH$_2$Cl$_2$ and the reaction mixture was then stirred for 1 h at −78° C. Triethylamine (4.3 mL, 30.9 mmol) was added and stirring was continued for 1 h. Following addition of saturated NH$_4$Cl (40 mL), the mixture was warmed to room temperature and the aqueous layer was extracted with two 40 mL portions of CH$_2$Cl$_2$. The combined organic layers were washed with saturated NaCl and dried over MgSO$_4$. Concentration in vacuo gave crude 2-(S)-6-(S) dibenzyl-4,4-diphenyl-4-sila-heptanedial. To this dialdehyde was added t-butanol (12.7 mL) followed by 5% NaH$_2$PO$_4$ (8.5 mL) and 1M KMnO$_4$ (12.7 mL). After stirring overnight at room temperature, 30 mL of saturated Na$_2$SO$_3$ solution was added and the pH was adjusted to 3 with cold (0° C.) 10% HCl to dissolve the colloidal MnO$_2$. The mixture was extracted with three 50 mL portions of ether, and the combined organic layers were extracted with 100 ml of 1N NaOH, The basic aqueous solution was then acidified with con HCl and extracted with three 100 mL portions of ether. The ether extracts were dried over MgSO$_4$ and concentration in vacuo gave crude diacid 55 (495 mg, 94% for two steps). The diacid was purified by recrystallization from CH$_2$Cl$_2$; $^1$H (300 MHz, CDCl$_3$) δ 7.45–6.80 (m, 20H), 2.80 (dd, 2H, J=12.6, 7.5Hz), 2.65–2.50 (m, 4H) 1.63 (dd, 2H, J=15, 7.2Hz), 1.34 (dd, 2H, J=15, 6 Hz); $^{13}$C (63 MHz, CDCl$_3$) δ 183.4, 138.5, 135.0, 134.2, 129.8, 128.9, 128.2, 128.1, 126.3, 42.3, 40.4, 14.7. HRMS (CI) calcd for C$_{32}$H$_{36}$NO$_4$Si (MNH$_4^+$): 526.2414. found: 526.2426.

Dibenzyl 2-(S)-6-(S)-dibenzyl-4,4-diphenyl-4-sila-heptanediamide (56) To a solution of 2-(S)-6-(S)dibenzyl-4,4-diphenyl-4-sila-heptanedioic acid 55 (228 mg, 0.45 mmol) in DMF (5 mL) at 0° C. was consecutively added in benzylamine (0.12 mL, 1.13 mmol), DPPA (0.24 mL, 1.13 mmol), and triethylamine (0.28 mL, 2.03 mmol). The reaction mixture was stirred at 0° C. for 2 h and then warmed to room temperature overnight. The mixture was diluted with 10 mL of ethyl acetate and washed successively with 5% aqueous HCl, water, saturated aqueous sodium bicarbonate, and saturated aqueous NaCl. After drying over $MgSO_4$ and filtering, the solution was concentrated in vacuo. Flash chromatography (7/3 hexane:ethyl acetate) afforded 56 as a foam (189 mg, 62%). $R_f$=0.26 (7/3 hexane:ethyl acetate); $^1H$ (250 MHz, $CDCl_3$) δ 7.47–6.79 (m, 30H), 5.56 (t, 2H), 4.31 (dd, 2H, J=14.7, 6.7 Hz), 3.82 (dd, 2H, J=14.7, 4.5 Hz), 2.87 (dd, 2H, J=13.2, 10.2Hz), 2.55 (dd, 2H, J=13.2, 4.7 Hz), 2.42 (m, 2H), 1.68 (dd, 2H, J=15.0, 7.4 Hz), 1.48 (dd, 2H, J=15.0, 6.6 Hz); $^{13}C$ (63 MHz, $CDCl_3$)δ 175.2, 139.8, 137.7, 135.4, 134.7, 129.7, 128.9. 128.5, 128.4, 128.1, 127.6, 127.2, 126.2, 45.3, 43.2, 41.5, 15.8. HRMS (FAB) calcd for $C_{46}H_{47}N_2O_2Si$: 687.3407. found: 687.3414.

Dibenzyl 2-(S)-6(S)-dibenzyl-4,4-dihydroxy-4-sila-heptanediamide (9a) To a solution of diamide 56 (141 mg, 0.2 mmol) in 8 mL $CH_2Cl_2$ at room temperature was added fresh distilled trifluoromethanesulfonic acid (0.2 mL, 2 mmol). After stirring at room temperature for 30 min the mixture was diluted with 80 mL $CH_2Cl_2$ and then transferred by cannula to another flask containing a 0° C. solution of $NaHCO_3$ (265 mg, 3 mmol) in 100 mL of water. The mixture was stirred for 30 min and organic phase was concentrated. The crude product was purified by preparative TLC (5/1 benzene:acetone) to give silanediol 9a (33 mg, 29%). $^1H$ NMR (250 Hz, $CDCl_3$) δ 7.16–6.70 (m, 20H), 6.53 (t, 2H, J=5.4 Hz), 4.13 (dd, 2H, J=14.9, 6.0 Hz), 3.80 (dd, 2H, J=14.9, 4.6 Hz), 2.98–2.60 (m, 6H), 1.08 (dd, 2H, J=15.6, 8.5 Hz), 0.86 (dd, 2H, J=15.6, 5.1 Hz); $^{13}C$ NMR (63 MHz, $CDCl_3$) δ 175.1, 139.4, 137.9, 129.1, 128.5, 128.3, 127.4, 127.1, 126.4, 43.6, 43.0, 41.5, 19.7.

Dibenzyl 2-(S)-6-(S)-dibenzyl-4,4-di(trimethylsilyloxy)-4-sila-heptanediamide (58) To a solution of silanediol 9a (58 mg, 0.08 mmol) in 3 mL $CH_2Cl_2$ at room temperature was added freshly distilled trifluoromethanesulfonic acid (0.07 mL, 0.8 mmol). After stirring at room temperature for 15 min, the mixture was diluted with 7 mL $CH_2Cl_2$ and then transferred via syringe to another flask containing a 0° C. mixture of $NH_4OH$ (1 mL) and water (9 mL). The mixture was stirred for 30 min. the organic layer was briefly dried over $Na_2SO_4$ and when concentrated gave crude silanediol 7 (46 mg). To a solution of this crude silanediol 7 (46 mg) in 10 mL of $CH_2Cl_2$ at room temperature was added triethylamine (0.17 mL, 15 eq) and chlorotrimethylsilane (0.1 mL, 10 eq). After stirring at room temperature for 1 h the mixture was concentrated in vacuo. Flash chromatography (7/1 hexane:ethyl acetate) gave 58 (23 mg, 40%); $^1H$ NMR (250 Hz, $CDCl_3$) δ 7.27–6.84 (m, 20H), 5.85 (t, 2h), 4.33 (dd, 2H, J=14.7, 6.6 Hz), 3.93 (dd, 2H, J=14.7, 4.6 Hz), 2.87 (mn, 4H), 2.56 (m,2H), 1.03 (dd, 2H, J=15, 7.2 Hz), 0.83 (dd, 2H, J=15, 7.2 Hz), 0.1 (s, 18H); HRMS (FAB) calcd for $C_{40}H_{54}N_2O_4NaSi_3$ (MNa+): 733.3289. found: 733.3311.

Preparation of symmetric compound 9a serves to demonstrate one approach to the synthesis of these silanediols. In particular, we used phenyl as a precursor for a silanol hydroxyl, a simple hydrolytic transformation that can be accomplished under the standard polypeptide deprotection conditions of strong acid. Phenyl is ideal here: stable to trifluoroacetic acid (TFA, conditions for removal of a Boc group) but is rapidly protodesilylated with trifluoromethanesulfonic acid (TfOH).

The $C_2$ symmetry of the HIV protease has led to the development of $C_2$ symmetric inhibitors such as Merck's L-700, 417. The silanediol analog 9a was prepared from the commercially available dichlorodiphenylsilane. Treatment of this dichlorosilane with the enantiomerically pure lithium reagent 53b led to the symmetric diether 54 in 75% yield. Cleavage of the ethers and oxidation to the diacid was followed by preparation of the diamide 56. For this study, N-benzyl amides were used as the simplest first analog. Hydrolysis of diphenylsilane 56 to the silanediol 9a was effected by treatment with triflic acid in dichloromethane at 0° C. for ten to 30 minutes. Under these conditions, both phenyl groups on silicon are lost very rapidly. We believe that the intermediate formed is not a di-triflate, but is the spirocyclic intermediate 57. Addition of the triflic acid-derived intermediate to an aqueous phase (either acidic, buffered, or basic) serves to finish hydrolysis to the diol 9a. Hydrolysis of 57 is expected, as five-membered ethers containing silicon are strained. The resulting diol 9a can be chromatographed on silica gel. The pure diol 9a is a solid and can be stored as a solid or in deuterochloroform solution for weeks without polymerization. We have proven the monomeric nature of 9a by capping the silanediol with chlorotrimethylsilane and triethylamine. The resulting trisiloxane 58 is stable to chromatography and is isolated in good yield (85%). Integration of the trimethylsilyl signals in the $^1H$ NMR provides a direct measurement of the silanol content of 9a. Based on $^{29}Si$ NMR chemical shift data, a sensitive indicator of both silicon substitution and valency, we find no evidence for an interaction of the carbonyl groups with the silicon in trisiloxane 58.

Protease Inhibition

The silanediol 9a was tested for inhibition of HIV-1 protease and was shown to inhibit the enzyme with an $IC_{50}$ value of 5.6 μM. The standard test procedure for HIV-1 protease inhibition uses recombinant HIV-1 protease in an assay which monitors cleavage of a substrate polypeptide using an HPLC-based detection system. Proc. Nat. Acad. Sci. 86, 9752 (1989).

Other uses for the compounds of the invention include as agricultural agents (herbicides, insecticides, nematocides, miticides), as agents for producing catalytic antibodies, and as building blocks for specialty materials such as biologically compatible polymers or as other polymer components such as silicone-reagents. We have shown the usefulness of these silanols as siloxane (silicone) components, see, e.g., compounds 39, 52, 58 and Schemes 4, 8 and 9.

Protease Inhibition and Antiviral Cell Culture Assay

Silanediol (9b) was tested against HIV-protease enzyme (Ki) and was also tested in an antiviral cell culture assay (IC90) (C. N. Hodge, et al., "Improved Cyclic Urea Inhibitors of the HIV-1 Protease: Synthesis, Potency, Resistance Profile, Human Pharmokinetics and X-ray Crystal Structure of DMP450", Chem. Biol. 3, 301–314 (1996) and compared with indinavir, an HIV protease inhibitor (Merck). The results were as follows:

| Compound | Ki | IC90 |
| --- | --- | --- |
| 9b | 2.7 nM | 170 nM |
| indinavir | 0.37 nM | 33 nM |

The compound of the invention, even in unoptimized form was similar to indinavir in effectiveness against HIV-1 protease and virus.

Dibenzyl 2-(S)-6-(S)-dibenzyl-4,4-dihydroxy-4-sila-heptanediamide (9a).

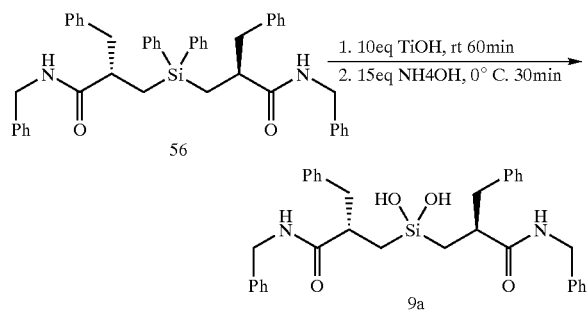

To a solution of diamide 56 (166.7 mg., 0.243 mmol) in 10 mL of $CH_2Cl_2$ at room temperature was added freshly distilled trifluoromethanesulfonic acid (0.22 mL, 2.43 mmol). After stirring at room temperature for 60 min, the mixture was cooled to 0° C. and 14.8 $NH_4OH$ (0.25 mL, 3.64 mmol) was added. The mixture was stirred at 0° C. for another 30 min then washed with 10 mL $H_2O$ (the aqueous layer was pH=8–9) and 10 mL brine. The organic layer was dried over $MgSO_4$ and filtered. The solution was concentrated to give silanediol 9a (13.7 mg, 0.243 mmol, 100%). When taken up in DMSO, compound 9a was fully stable for one week.

Silanediol Dimer (60)

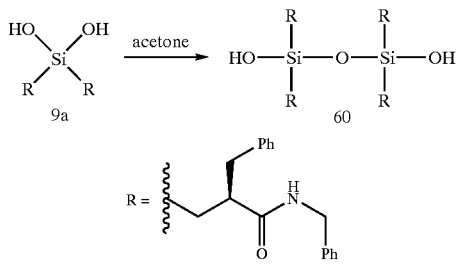

Silanediol 9a was taken up in acetone and left for one week at room temperature. Analysis of solution found that starting silanediol had become a mixture of dimer 60 and tetramer 61 in a ratio of 2:1.

Cyclic Silanediol Tetramer (61)

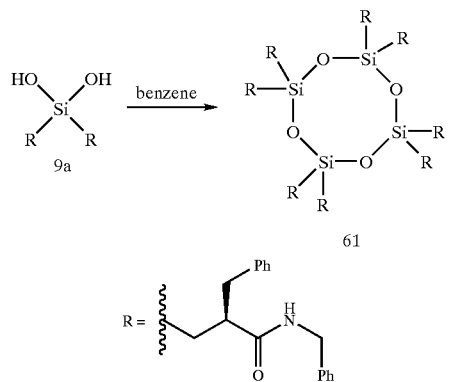

Silanediol 9a was taken up in benzene and left for one week at room temperature. Analysis of solution found that starting silanediol had become cyclic tetramer 61 quantitatively.

Protease Inhibition

Compounds 9a, 60, and 61 were tested against HIV-protease enzyme (Ki) as described above. The results were as follows:

| Compound | Ki |
| --- | --- |
| 9a | 3161 nM |
| 60 | 4667 nM |
| 61 | 2302 nM |

In view of the general presumption that siloxanes are chemically very stable, and that 60 and 61 would not be expected to fit an enzyme active site, it is surprising that 9a, 60, and 61 are very similar in their level of inhibition of the HIV protease. While it is not intended to be bound by theory, one possible explanation for this phenomena is that 60 and 61 hydrolyze to 9a under aqueous conditions of the enzyme assay. Hydrolysis of siloxanes under aqueous environmental conditions has been described. Carpenter, J. C.; Cella, J. A.; Dorn S. B. "Study of the Degradation of Polydimethylsiloxanes on Soil," *Environ. Sci. Technol.* 1995, 29, 864–868. Humans and other biological organisms are largely aqueous entities, and therefore administering the siloxanes in formulas II and III, for which 60 and 61 are exemplary, will be equivalent to administering the compound of formula I for which 9a is exemplary.

What is claimed is:

1. A compound of formula III

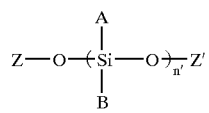

formula III in which

Z and Z' are independently H, a lower alkyl, or $Q_3Si$ where Q is a lower alkyl, or Q is an aryl of four to ten carbon atoms n' is 2–50;

each of A and B is independently a) a $C_3$–$C_{10}$ alkyl or a substituent obtained by substituting at least one carbon atom of a $C_3$–$C_{10}$ alkyl group with a heteroatom, b) an aryl of four to seven carbons or heteroatoms, c) a cyclic of three to ten carbons or heteroatoms, or moieties of the formulas

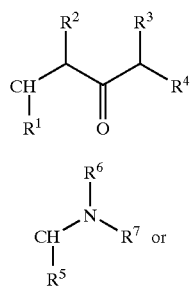

d)

e)

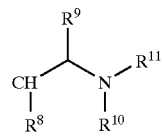

f)

wherein in d), e) and f), CH is bonded to silicon;

wherein $R^1$ to $R^{11}$ are independently hydrogen, alkyl of 1 to 10 carbons or heteroatoms, aryl of 4 to 14 carbons or heteroatoms, arylalkyl of 5 to 20 carbons or heteroatoms, substituted carbonyl or unsubstituted carbonyl;

wherein said heteroatoms is selected from the group consisting of nitrogen, oxygen, silicon and sulfur; and wherein at least one of A and B, or both A and B are selected from the group consisting of d), e) and f).

2. A compound according to claim 1 wherein moieties for $R^3$, $R^4$, $R^6$, $R^7$, $R^{10}$ and $R^{11}$ include at least one amino acid.

3. A composition comprising a compound of claim 1 and a pharmaceutically acceptable carrier.

* * * * *

UNITED STATES PATENT AND TRADEMARK OFFICE
CERTIFICATE OF CORRECTION

PATENT NO.        : 6,960,678 B2
APPLICATION NO. : 10/171560
DATED              : November 1, 2005
INVENTOR(S)       : Sieburth et al.

It is certified that error appears in the above-identified patent and that said Letters Patent is hereby corrected as shown below:

IN THE CLAIMS:

Claim 1, in the Formula labeled "d)":

Now reads:

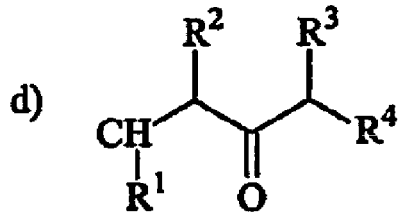

Should read:

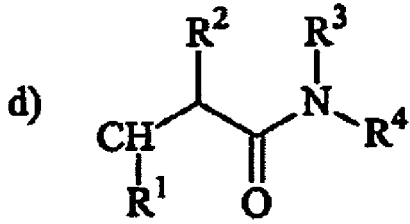

UNITED STATES PATENT AND TRADEMARK OFFICE
CERTIFICATE OF CORRECTION

PATENT NO. : 6,960,678 B2
APPLICATION NO. : 10/171560
DATED : November 1, 2005
INVENTOR(S) : Sieburth et al.

It is certified that error appears in the above-identified patent and that said Letters Patent is hereby corrected as shown below:

IN THE CERTIFICATE OF CORRECTION:

ON THE COVER PAGE:

In (74) Attorney, Agent of Firm:   Now reads:   "Hoffman & Baron, LLP"

Should read:   --Hoffmann & Baron, LLP--

Signed and Sealed this

Twenty-eighth Day of November, 2006

JON W. DUDAS
*Director of the United States Patent and Trademark Office*